(12) United States Patent
Hitomi et al.

(10) Patent No.: US 11,702,578 B2
(45) Date of Patent: *Jul. 18, 2023

(54) THERMALLY CONDUCTIVE MATERIAL, DEVICE WITH THERMALLY CONDUCTIVE LAYER, COMPOSITION FOR FORMING THERMALLY CONDUCTIVE MATERIAL, AND DISK-LIKE LIQUID CRYSTAL COMPOUND

(71) Applicant: FUJIFILM Corporation, Tokyo (JP)

(72) Inventors: Seiichi Hitomi, Ashigara-kami-gun (JP); Keita Takahashi, Ashigara-kami-gun (JP); Teruki Niori, Ashigara-kami-gun (JP); Yuji Yoshida, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 522 days.

This patent is subject to a terminal disclaimer.

(21) Appl. No.: 16/741,286

(22) Filed: Jan. 13, 2020

(65) Prior Publication Data
US 2020/0148931 A1 May 14, 2020

Related U.S. Application Data

(63) Continuation of application No. PCT/JP2018/026388, filed on Jul. 12, 2018.

(30) Foreign Application Priority Data

Jul. 14, 2017 (JP) ................................. 2017-138210
Dec. 27, 2017 (JP) ................................. 2017-252056

(51) Int. Cl.
| | |
|---|---|
| *C09K 5/14* | (2006.01) |
| *C07C 43/23* | (2006.01) |
| *C07C 69/88* | (2006.01) |
| *C07C 223/06* | (2006.01) |
| *C07C 261/02* | (2006.01) |
| *C07C 321/26* | (2006.01) |
| *C07C 323/52* | (2006.01) |
| *C07D 271/10* | (2006.01) |
| *C07D 303/12* | (2006.01) |
| *C07D 307/89* | (2006.01) |
| *C08G 59/24* | (2006.01) |
| *C08G 59/40* | (2006.01) |
| *C08G 59/42* | (2006.01) |
| *C08G 59/50* | (2006.01) |
| *C08G 59/62* | (2006.01) |
| *C08G 65/40* | (2006.01) |

(Continued)

(52) U.S. Cl.
CPC .............. *C09K 5/14* (2013.01); *C07C 43/23* (2013.01); *C07C 69/88* (2013.01); *C07C 223/06* (2013.01); *C07C 261/02* (2013.01); *C07C 321/26* (2013.01); *C07C 323/52* (2013.01); *C07D 271/10* (2013.01); *C07D 303/12* (2013.01); *C07D 307/89* (2013.01); *C08G 59/245* (2013.01); *C08G 59/4014* (2013.01); *C08G 59/423* (2013.01); *C08G 59/4238* (2013.01); *C08G 59/504* (2013.01); *C08G 59/5046* (2013.01); *C08G 59/621* (2013.01); *C08G 65/40* (2013.01); *C08J 5/18* (2013.01); *C08K 3/38* (2013.01); *C08J 2363/00* (2013.01); *C08J 2371/10* (2013.01); *C08K 2003/385* (2013.01); *C08K 2201/001* (2013.01); *H01L 23/3737* (2013.01)

(58) Field of Classification Search
CPC . C09K 5/14; C09K 5/08; C09K 19/04; C09K 2019/0429; C08K 3/38; C08K 3/22; C08K 13/02; C08K 2201/001; C08K 2003/385; C08G 59/245; C08J 5/18; C08J 2363/00; C08J 237/10; H01L 23/3737
See application file for complete search history.

(56) References Cited

U.S. PATENT DOCUMENTS

| | | |
|---|---|---|
| 5,635,105 A | 6/1997 | Kawata et al. |
| 2004/0147709 A1 | 7/2004 | Akatsuka et al. |

(Continued)

FOREIGN PATENT DOCUMENTS

| | | |
|---|---|---|
| CN | 102924925 A | 2/2013 |
| CN | 105733608 A | 7/2016 |

(Continued)

OTHER PUBLICATIONS

Kang et al. "Heat Transfer Organic Materials: Robust Polymer Films with the Outstanding Thermal Conductivity Fabricated by the Photopolymerization of Uniaxially Oriented Reactive Discongens", ACS Applied Materials and Interfaces, vol. 8, No. 44, Nov. 9, 2016, pp. 30492-30501.

(Continued)

*Primary Examiner* — Jane L Stanley
(74) *Attorney, Agent, or Firm* — Sughrue Mion, PLLC

(57) ABSTRACT

The present invention provides a thermally conductive material having excellent thermal conductivity. Furthermore, the present invention provides a device with a thermally conductive layer that has a thermally conductive layer containing the thermally conductive material and a composition for forming a thermally conductive material that is used for forming the thermally conductive material. The thermally conductive material according to an embodiment of the present invention contains a cured substance of a disk-like compound, which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups.

16 Claims, No Drawings

(51) Int. Cl.
  *C08J 5/18* (2006.01)
  *C08K 3/38* (2006.01)
  *H01L 23/373* (2006.01)

(56) References Cited

U.S. PATENT DOCUMENTS

| | | | |
|---|---|---|---|
| 2006/0159866 A1* | 7/2006 | Ito | G02B 5/3016 428/1.3 |
| 2008/0186443 A1* | 8/2008 | Nishikawa | G02B 5/3016 252/299.61 |
| 2010/0239788 A1 | 9/2010 | Hamasaki et al. | |
| 2018/0120652 A1 | 5/2018 | Lan et al. | |
| 2018/0327586 A1 | 11/2018 | Takahashi | |

FOREIGN PATENT DOCUMENTS

| | | |
|---|---|---|
| DE | 19517762 A1 | 11/1995 |
| JP | 7-316257 A | 12/1995 |
| JP | 11-323162 A | 11/1999 |
| JP | 2001-004837 A | 1/2001 |
| JP | 4118691 B2 | 7/2008 |
| JP | 2009-221124 A | 10/2009 |
| JP | 2010-138283 A | 6/2010 |
| JP | 2010-244038 A | 10/2010 |
| JP | 6625669 B2 | 12/2019 |
| KR | 10-2012-0106623 A | 9/2012 |
| WO | 2017/131007 A1 | 8/2017 |

OTHER PUBLICATIONS

Kim et al. "Highly anisotropic thermal conductivity of discotic nematic liquid crystalline films with homeotropic alignment", Chemical Communications, vol. 53, No. 58, Jun. 26, 2017, pp. 8227-8230.
International Search Report dated Oct. 16, 2018 from the International Searching Authority in International Application No. PCT/JP2018/026388.
Written Opinion dated Oct. 16, 2018 from the International Bureau in International Application No. PCT/JP2018/026388.
International Preliminary Report on Patentability dated Jan. 14, 2020 from the International Bureau in International Application No. PCT/JP2018/026388.
Communication dated Feb. 24, 2021 in corresponding Japanese Application No. 2019-529790.
Communication dated Apr. 9, 2021, from the European Patent Office in European Application No. 20203834.5.
Partial Supplementary European Search Report dated May 11, 2020, from the European Patent Office in Application No. 18831796.0.
Office Action dated Feb. 7, 2022 from the China National Intellectual Property Administration in CN application No. 201880046559.4.
Notification of Reason for Refusal dated Jan. 11, 2021 from the Korean Intellectual Property Office in KR Application No. 10-2020-7001108.
Notice of Reasons for Refusal dated Sep. 5, 2022 from The State Intellectual Property Office of the P.R. of China in Chinese Application No. 201880046559.4.

* cited by examiner

THERMALLY CONDUCTIVE MATERIAL, DEVICE WITH THERMALLY CONDUCTIVE LAYER, COMPOSITION FOR FORMING THERMALLY CONDUCTIVE MATERIAL, AND DISK-LIKE LIQUID CRYSTAL COMPOUND

CROSS-REFERENCE TO RELATED APPLICATIONS

This application is a Continuation of PCT International Application No. PCT/JP2018/026388 filed on Jul. 12, 2018, which claims priority under 35 U.S.C. § 119(a) to Japanese Patent Application No. 2017-138210 filed on Jul. 14, 2017 and Japanese Patent Application No. 2017-252056 filed on Dec. 27, 2017. Each of the above applications is hereby expressly incorporated by reference, in its entirety, into the present application.

BACKGROUND OF THE INVENTION

1. Field of the Invention

The present invention relates to a thermally conductive material, a device with a thermally conductive layer, a composition for forming a thermally conductive material, and a disk-like liquid crystal compound.

2. Description of the Related Art

In recent years, power semiconductor devices used in various electrical instruments such as personal computers, general home appliances, and automobiles have been rapidly downsized. The control of heat generated from the power semiconductor devices, which have been highly integrated as a result of downsizing, has become an issue.

In order to resolve such an issue, thermally conductive materials promoting dissipation of heat from the power semiconductor devices are used (JP1999-323162A (JP-H11-323162A) and Japanese Patent No. 411691).

SUMMARY OF THE INVENTION

As a result of examining the techniques disclosed in JP1999-323162A (JP-H11-323162A) and Japanese Patent No. 411691, the inventors of the present invention have found that the thermal conductivity of the thermally conductive materials disclosed in the documents have not necessarily reached the required level.

An object of the present invention is to provide a thermally conductive material having excellent thermal conductivity.

Another object of the present invention is to provide a device with a thermally conductive layer that has a thermally conductive layer containing the thermally conductive material and a composition for forming a thermally conductive material that is used for forming the thermally conductive material.

Still another object of the present invention is to provide a novel disk-like liquid crystal compound.

As a result of conducting intensive examinations, the inventors of the present invention have found that the above objects can be achieved using a disk-like compound having a predetermined group, and accomplished the present invention.

That is, the inventors have found that the above objects can be achieved by the following constitution.

[1] A thermally conductive material containing a cured substance of a disk-like compound, which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups.

[2] The thermally conductive material described in [1], in which the disk-like compound is represented by Formula (1) which will be described later.

[3] The thermally conductive material described in [2], in which the disk-like compound is a compound represented by Formula (D4) which will be described later.

[4] The thermally conductive material described in any one of [1] to [3], in which the number of the reactive functional groups the disk-like compound has is 3 to 6.

[5] The thermally conductive material described in any one of [1] to [4], in which the disk-like compound has 3 to 6 groups selected from the group consisting of a hydroxyl group, a carboxylic acid group, and a carboxylic acid anhydride group.

[6] The thermally conductive material described in any one of [1] to [5], in which the crosslinking compound is an epoxy compound.

[7] The thermally conductive material described in [6], in which the epoxy compound is a compound represented by Formula (E1) which will be described later or a disk-like compound having an epoxy group.

[8] The thermally conductive material described in any one of [1] to [7], further containing an inorganic substance.

[9] The thermally conductive material described in [8], in which the inorganic substance is an inorganic nitride or an inorganic oxide.

[10] The thermally conductive material described in [8] or [9], in which the inorganic substance is boron nitride.

[11] The thermally conductive material described in any one of [1] to [10] that is in the form of a sheet.

[12] A device with a thermally conductive layer having a device and a thermally conductive layer which is disposed on the device and contains the thermally conductive material described in any one of [1] to [11].

[13] A composition for forming a thermally conductive material containing a disk-like compound, which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups.

[14] The composition for forming a thermally conductive material described in [13] that exhibits liquid crystallinity, containing a disk-like liquid crystal compound, which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups.

[15] A disk-like liquid crystal compound having one or more reactive functional groups selected from the group consisting of a hydroxyl group, a carboxylic acid group, a carboxylic acid anhydride group, an amino group, a cyanate ester group, and a thiol group.

[16] The disk-like liquid crystal compound described in [15] that is represented by Formula (1A) which will be described later.

[17] The disk-like liquid crystal compound described in [15] or [16] that is a compound represented by Formula (D4A) which will be described later or a compound represented by Formula (D16) which will be described later.

[18] The disk-like liquid crystal compound described in any one of [15] to [17], in which each of the reactive functional groups is a group selected from the group consisting of a hydroxyl group, a carboxylic acid group, and a carboxylic acid anhydride group.

[19] The disk-like liquid crystal compound described in any one of [15] to [18] that has a phase transition temperature, at which transition from a crystal phase to a liquid crystal phase occurs, equal to or lower than 180° C.

According to the present invention, it is possible to provide a thermally conductive material having excellent thermal conductivity.

Furthermore, according to the present invention, it is possible to provide a device with a thermally conductive layer that has a thermally conductive layer containing the thermally conductive material and a composition for forming a thermally conductive material that is used for forming the thermally conductive material.

In addition, according to the present invention, it is possible to provide a novel disk-like liquid crystal compound.

DESCRIPTION OF THE PREFERRED EMBODIMENTS

Hereinafter, a thermally conductive material, a device with a thermally conductive layer, a composition for forming a thermally conductive material (hereinafter, simply referred to as "present composition" as well), and a disk-like liquid crystal compound according to an embodiment of the present invention will be specifically described.

Hereinafter, constituents will be described based on typical embodiments of the present invention in some cases, but the present invention is not limited to the embodiments.

In the present specification, a range of numerical values described using "to" means a range including the numerical values listed before and after "to" as a lower limit and an upper limit.

In the present specification, the description of "(meth) acryloyl group" means "either or both of the acryloyl group and methacryloyl group".

In the present specification, the description of "(meth) acrylamide group" means "either or both of the acrylamide group and methacrylamide group".

In the present specification, in a case where the description of "which may have a substituent" appears, the type of the substituent, the position of the substituent, and the number of substituents are not particularly limited. For example, the number of substituents may be 1, 2, or greater. Examples of the substituent include a group of monovalent non-metal atoms excluding hydrogen atoms. For example, the substituent can be selected from the following substituent group Y.

Substituent Group Y:

a halogen atom (—F, —Br, —Cl, —I), a hydroxyl group, an amino group, a carboxylic acid group and a conjugate base group thereof, a carboxylic acid anhydride group, a cyanate ester group, an unsaturated polymerizable group, an oxiranyl group, an oxetanyl group, an aziridinyl group, a thiol group, an isocyanate group, a thioisocyanate group, an aldehyde group, an alkoxy group, an aryloxy group, an alkylthio group, an arylthio group, an alkyldithio group, an aryldithio group, a N-alkylamino group, a N,N-dialkylamino group, a N-arylamino group, a N,N-diarylamino group, a N-alkyl-N-arylamino group, an acyloxy group, a carbamoyloxy group, a N-alkylcarbamoyloxy group, a N-arylcarbamoyloxy group, a N,N-dialkylcarbamoyloxy group, a N,N-diarylcarbamoyloxy group, a N-alkyl-N-arylcarbamoyloxy group, an alkylsulfoxy group, an arylsulfoxy group, an acylthio group, an acylamino group, a N-alkylacylamino group, a N-arylacylamino group, a ureide group, a N'-alkylureide group, a N',N'-dialkylureide group, a N'-arylureide group, a N',N'-diarylureide group, a N'-alkyl-N'-arylureide group, a N-alkylureide group, a N-arylureide group, a N'-alkyl-N-alkylureide group, a N'-alkyl-N-arylureide group, a N',N'-dialkyl-N-alkyluriede group, N',N'-dialkyl-N-arylureide group, a N'-aryl-N-alkylureide group, a N'-aryl-N-arylureide group, N',N'-daryl-N-alkylureide group, a N',N'-diaryl-N-arylureide group, a N'-alkyl-N'-aryl-N-alkylureide group, a N'-alkyl-N'-aryl-N-arylureide group, an alkoxycarbonylamino group, an aryloxycarbonylamino group, a N-alkyl-N-alkoxycarbonylamino group, a N-alkyl-N-aryloxycarbonylamino group, a N-aryl-N-alkoxycarbonylamino group, a N-aryl-N-aryloxycarbonylamino group, a formyl group, an acyl group, an alkoxycarbonyl group, an aryloxycarbonyl group, a carbamoyl group, a N-alkylcarbamoyl group, a N,N-dialkylcarbamoyl group, a N-arylcarbamoyl group, a N,N-diarylcarbamoyl group, a N-alkyl-N-arylcarbamoyl group, an alkylsulfinyl group, an arylsulfinyl group, an alkylsulfonyl group, an arylsulfonyl group, a sulfo group (—$SO_3H$) and a conjugate base group thereof, an alkoxysulfonyl group, an aryloxysulfonyl group, a sulfinamoyl group, a N-alkylsulfinamoyl group, a N,N-dialkylsulfinamoyl group, a N-arylsulfinamoyl group, a N,N-diarylsulfinamoyl group, a N-alkyl-N-arylsulfinamoyl group, a sulfamoyl group, a N-alkylsulfamoyl group, a N,N-dialkylsulfamoyl group, a N-arylsulfamoyl group, a N,N-diarylsulfamoyl group, a N-alkyl-N-arylsulfamoyl group, a N-acylsulfamoyl group and a conjugate base group thereof, a N-alkylsulfonylsulfamoyl group (—$SO_2NHSO_2$ (alkyl)) and a conjugate base group thereof, a N-arylsulfonylsulfamoyl group (—$SO_2NHSO_2$ (aryl)) and a conjugate base group thereof, a N-alkylsulfonylcarbamoyl group (—$CONHSO_2$ (alkyl)) and a conjugate base group thereof, a N-arylsulfonylcarbamoyl group (—$CONHSO_2$ (aryl)) and a conjugate base group thereof, an alkoxysilyl group (—Si (Oalkyl)$_3$)), an aryloxysilyl group (—Si(Oaryl)$_3$)), a hydroxysilyl group (—Si(OH)$_3$) and a conjugate base group thereof, a phosphono group (—$PO_3H_2$) and a conjugate base group thereof, a dialkylphosphono group (—$PO_3$(alkyl)$_2$), a diarylphosphono group (—$PO_3$(aryl)$_2$), an alkylarylphosphono group (—$PO_3$(alkyl)(aryl)), a monoalkylphosphono group ($PO_3H$(alkyl)) and a conjugate base group thereof, a monoarylphospho group (—$PO_3H$(aryl)) and a conjugate base group thereof, a phosphonooxy group (—$OPO_3H_2$) and a conjugate base group thereof, a dialkylphosphonooxy group ($OPO_3$(alkyl)$_2$), a diarylphosphonooxy group (—$OPO_3$(aryl)$_2$), an alkylarylphosphonooxy group (—$OPO_3$(alkyl)(aryl)), a monoalkylphosphonooxy group (—$OPO_3H$(alkyl)) and a conjugate base group thereof, a monoarylphosphonooxy group (—$OPO_3H$(aryl)) and a conjugate base group thereof, a cyano group, a nitro group, an aryl group, an alkenyl group, an alkynyl group, and an alkyl group.

If possible, these substituents may form a ring by being bonded to each other or by being bonded to the group substituted with the substituents.

Examples of the unsaturated polymerizable group include a (meth)acryloyl group, a (meth)acrylamide group, and substituents represented by Q1 to Q7 shown below.

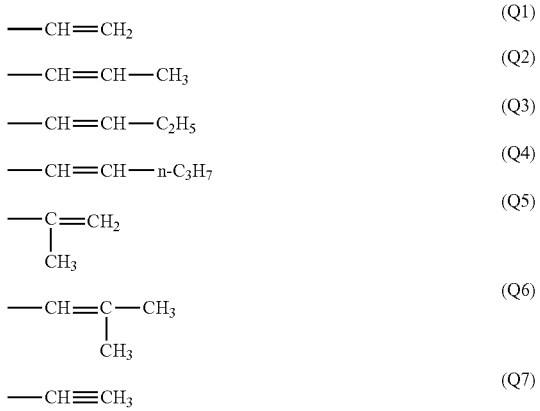

[Thermally Conductive Material]

The thermally conductive material according to an embodiment of the present invention contains a cured substance of a disk-like compound (hereinafter, referred to as "specific disk-like compound" as well), which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups (hereinafter, simply referred to as "crosslinking compound" as well). That is, the thermally conductive material according to the embodiment of the present invention contains a cured substance obtained by reacting the specific disk-like compound and the crosslinking compound with each other.

The inventors of the present invention have found that in case where the specific disk-like compound and the crosslinking compound are used, the thermal conductivity of the thermally conductive material can be improved.

The mechanism is unclear. Presumably, while the rod-like compound described in JP1999-323162A (JP-H11-323162A) and Japanese Patent No. 411691 can only linearly (one-dimensionally) conduct heat, the cured substance of the specific disk-like compound can conduct heat in a normal direction of the disk-like structure thereof, and accordingly, thermal conduction paths may increase, and the thermal conductivity may be improved.

Hereinafter, first, the specific disk-like compound and the crosslinking compound used for obtaining the cured substance contained in the thermally conductive material will be specifically described.

[Specific Disk-Like Compound]

Examples of raw materials of the cured substance contained in the thermally conductive material include the specific disk-like compound.

In the present specification, a disk-like compound means a compound having a disk-like structure in at least a portion thereof. By the disk-like structure, the disk-like compound can establish a columnar structure by forming a stacking structure. As the disk-like compound, a compound is preferable which has at least an aromatic ring and can establish a columnar structure by forming a stacking structure based on the intermolecular π-π interaction.

It is considered that such a columnar structure may promote the thermal conduction in the normal direction of the disk-like structure as described above and contribute to the improvement of thermal conductivity.

The specific disk-like compound has one or more reactive functional groups selected from the group consisting of a hydroxyl group (—OH), a carboxylic acid group (—COOH), a carboxylic acid anhydride group, an amino group (—NH$_2$), a cyanate ester group (—O—C≡N), and a thiol group (—SH).

Particularly, from the viewpoint of further improving the thermal conductivity of the thermally conductive material, the specific disk-like compound preferably has one or more reactive functional groups selected from the group consisting of a hydroxyl group, a carboxylic acid group, a carboxylic acid anhydride group, an amino group, and a cyanate ester group, and more preferably has one or more reactive functional groups selected from the group consisting of a hydroxyl group, a carboxylic acid group, and a carboxylic acid anhydride group.

Furthermore, from the viewpoint of further improving the thermal conductivity of the thermally conductive material, the specific disk-like compound preferably has 3 to 8 reactive functional groups, and more preferably has 3 to 6 reactive functional groups.

Particularly, the specific disk-like compound preferably has 3 to 8 reactive functional groups selected from the group consisting of a hydroxyl group, a carboxylic acid group, and a carboxylic acid anhydride group, and more preferably has 3 to 6 reactive functional groups selected from the group described above.

The cured substance of the specific disk-like compound having 3 or more reactive functional groups has a high glass transition temperature and exhibits excellent heat resistance.

As the hydroxyl group, a hydroxyl group is preferable which is directly bonded to an aromatic ring such as a phenyl group.

The carboxylic acid anhydride group means a monovalent substituent obtained by removing any hydrogen atom from an acid anhydride such as a maleic acid anhydride, a phthalic acid anhydride, a pyromellitic acid anhydride, and a trimellitic acid anhydride.

The disk-like compound may be a liquid crystal compound that exhibits liquid crystallinity or a non-liquid crystal compound that does not exhibit liquid crystallinity. From the viewpoint of further improving the thermal conductivity of the thermally conductive material (particularly, from the viewpoint of further improving the thermal conductivity in a case where the thermally conductive material is made into a thicker film (for example, having a thickness equal to or greater than 400 μm)), a liquid crystal compound is preferable. That is, as the disk-like compound, a disk-like liquid crystal compound is preferable.

Presumably, in the cured substance of the specific disk-like compound and the crosslinking compound, a plurality of domains may be formed according to the orientation order parameter, and there may be a plurality of boundaries (grain boundaries) between the domains. It is considered that in a case where the specific disk-like compound is a disk-like liquid crystal compound, the size of the domains could be further increased (in other words, the number of grain boundaries could be reduced), and consequently, particularly in a case where the cured substance is made into a thick film, the thermal conductivity of the cured substance could be further improved.

The liquid crystallinity of the specific disk-like compound can be checked by observation using a polarizing microscope or by differential scanning calorimetry.

Specific examples of the disk-like compound include the compounds described in C. Destrade et al., Mol. Crysr. Liq. Cryst., vol. 71, page 111 (1981); The Chemical Society of Japan, Quarterly Review of Chemistry, No. 22, Chemistry of Liquid Crystal, chapter 5, paragraph 2 of chapter 10 (1994); B. Kohne et al., Angew, Chem. Soc. Chem. Comm., page 1794 (1985); J. Zhang et al., J. Am. Chem. Soc., vol. 116, page 2655 (1994); and JP4592225B. Examples of the disk-like compound include the triphenylene structure described in Angew. Chem. Int. Ed. 2012, 51, 7990-7993 or JP1995-306317A (JP-H07-306317A), the trisubstituted benzene structure described in JP2007-002220A or JP2010-244038A, and the like.

Examples of the specific disk-like compound include a compound represented by Formula (1).

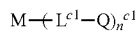
(1)

In the formula, M represents an $n^{c1}$ valent disk-like core portion.

$L^{c1}$ represents a divalent linking group.

Q represents a hydrogen atom or a substituent.

$n^{c1}$ represents an integer equal to or greater than 3.

Here, one or more Q's represent the reactive functional groups.

The disk-like core portion represented by M is not particularly limited. Examples thereof include structures represented by Formulae (CR1) to (CR16). * represents a position of binding to a group represented by -$L^{c1}$-Q. In (CR16), $A^{2X}$, $A^{3X}$, and $A^{4X}$ each independently represent —CH= or N=. It is preferable that all the $A^{2X}$, $A^{3X}$, and $A^{4X}$ represent —CH=.

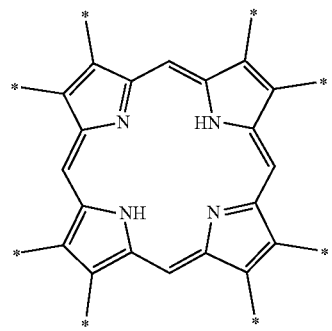
(CR1)

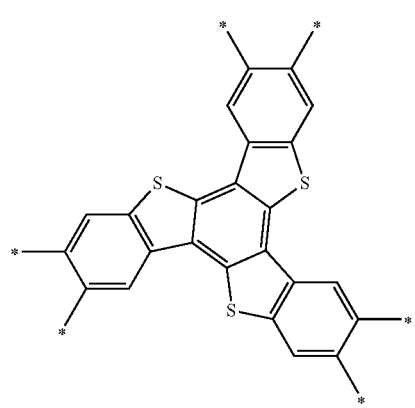
(CR2)

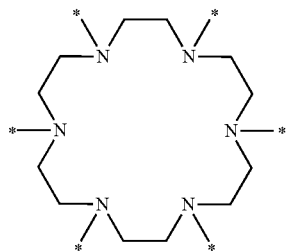
(CR3)

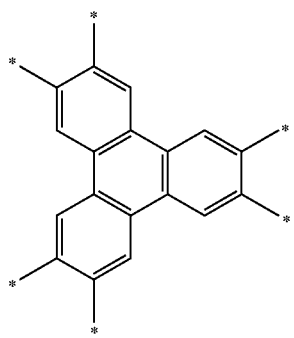
(CR4)

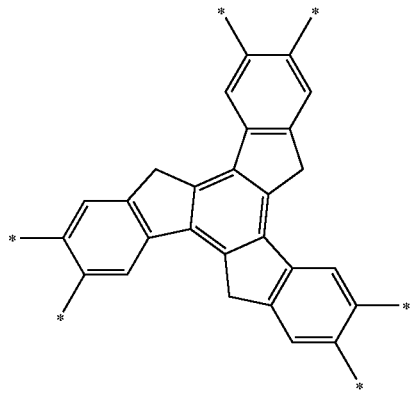
(CR5)

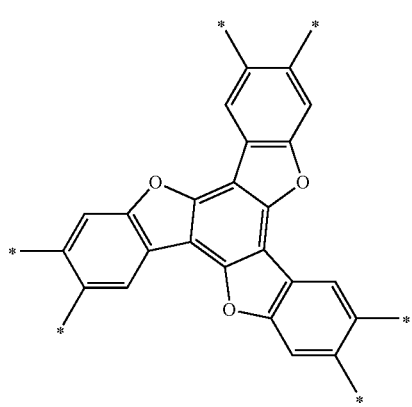
(CR6)

(CR7)
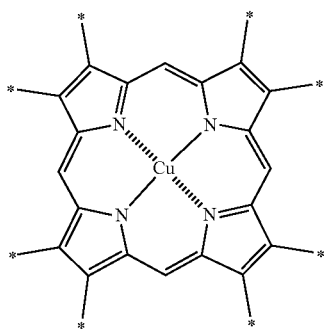
(CR8)
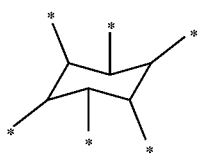
(CR9)
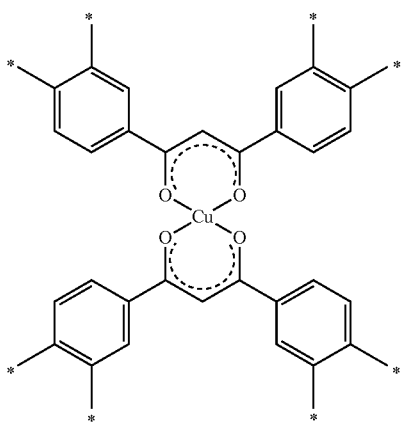
(CR10)
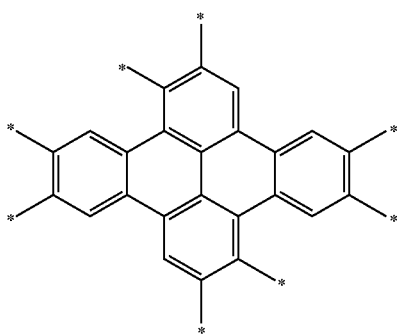
(CR11)
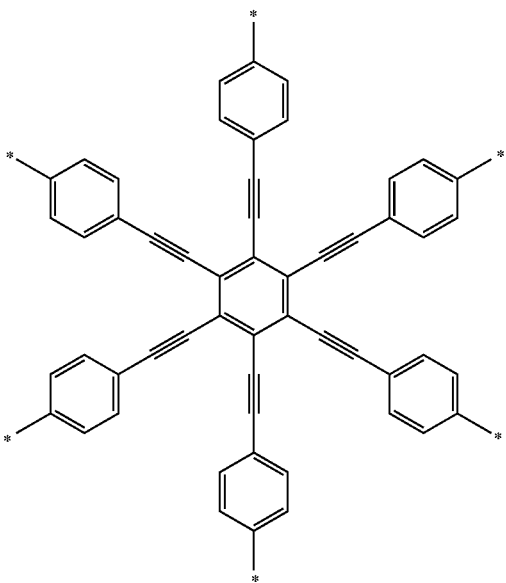
(CR12)

-continued (CR13)
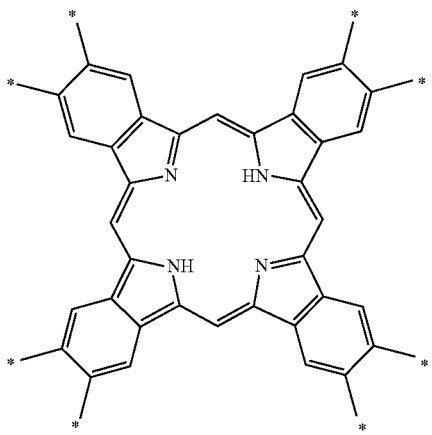

(CR14)
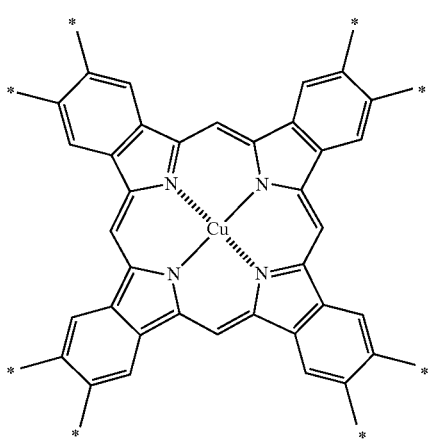

(CR15)
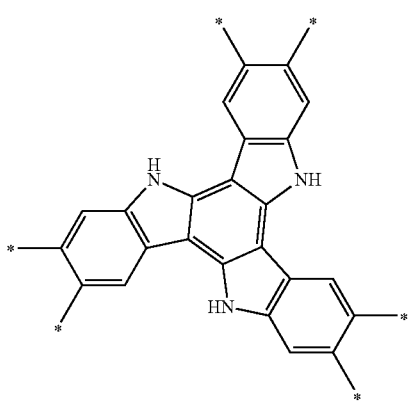

(CR16)
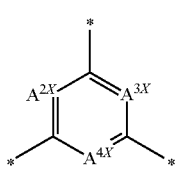

$L^{c1}$ represents a divalent linking group.

From the viewpoint of further improving the thermal conductivity of the thermally conductive material, $L^{c1}$'s preferably each independently represent a group selected from the group consisting of an alkylene group, an alkenylene group, an arylene group, a heteroarylene group, —C(═O)—, —NR$^{c1}$—, —O—, —S—, and a combination of these, and more preferably each independently represent a group obtained by combining two or more groups selected from the group consisting of an alkylene group, an alkenylene group, an arylene group, a heteroarylene group, —C(═O)—, —NR$^{c1}$—, —O—, and —S—.

$R^{c1}$ represents a hydrogen atom or an alkyl group. The number of carbon atoms in the alkyl group represented by $R^{c1}$ is preferably 1 to 12, and more preferably 1 to 3.

The number of carbon atoms in the alkylene group is preferably 1 to 12.

The number of carbon atoms in the alkenylene group is preferably 2 to 12.

The number of carbon atoms in the arylene group is preferably equal to or smaller than 10, and more preferably 6.

The number of carbon atoms in the heteroarylene group is preferably equal to or smaller than 6. The heteroarylene group is preferably a 5-membered ring or a 6-membered ring. The heteroatom contained in the heteroarylene group is not particularly limited, and examples thereof include a nitrogen atom, an oxygen atom, a sulfur atom, and the like. The number of heteroatoms in the heteroarylene group is not particularly limited, but is preferably 1 to 3 for example.

The alkylene group, the alkenylene group, the arylene group, and the heteroarylene group may have a substituent (preferably an alkyl group, a halogen atom, cyano, an alkoxy group, an acyloxy group, and the like).

In a case where M is a triphenylene skeleton represented by Formula (CR4), from the viewpoint of further improving the thermal conductivity of the thermally conductive material by causing the disk-like compound to express liquid crystallinity, $L^{c1}$ preferably represents a divalent linking group having a partial structure represented by *$^{c1}$-alkylene group-$X^{c1}$-*$^{c2}$, *$^{c1}$-$X^{c1}$-alkylene group-*$^{c2}$, or *$^{c1}$-$X^{c1}$-arylene group-O-*$^{c2}$.

$X^{c1}$ represents —O—C(═O)— or —C(═O)—O—.

*$^{c1}$ represents a position of binding to the disk-like core portion, and *$^{c2}$ represents the other binding position.

Q's each independently represent a hydrogen atom or a substituent.

Examples of the substituent include the groups exemplified in the substituent group Y described above. More specifically, examples of the substituent include the reactive functional group described above, a halogen atom, an isocyanate group, a cyano group, an unsaturated polymerizable group, an oxiranyl group, an oxetanyl group, an aziridinyl group, a thioisocyanate group, an aldehyde group, and a sulfo group.

In Formula (1), one or more Q's represent the reactive functional group. Particularly, from the viewpoint of further improving the thermal conductivity of the thermally conductive material, it is preferable that all the Q's represent the reactive functional group.

$n^{c1}$ represents an integer equal to or greater than 3. From the viewpoint of further improving the thermal conductivity of the thermally conductive material, $n^{c1}$ is preferably 3 to 8, and more preferably 3 to 6.

From the viewpoint of further improving the thermal conductivity of the thermally conductive material, as the specific disk-like compound, a compound represented by any of the following Formulae (D1) to (D16) is preferable.

In the following formulae, "-LQ" represents "-L-Q-", and "QL-" represents "Q-L-".

First, Formulae (D1) to (D15) will be specifically described.

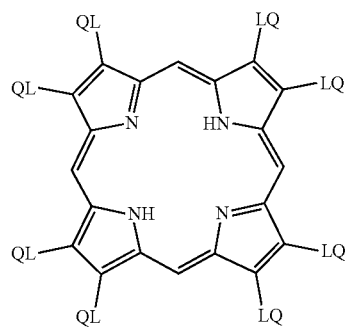
(D1)
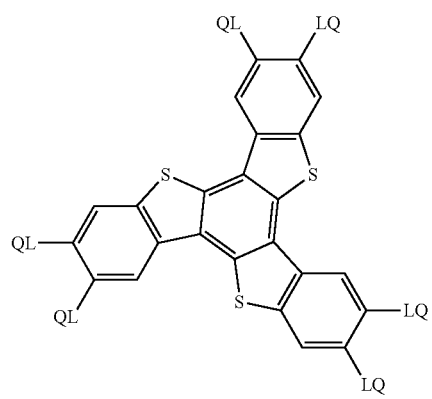
(D2)
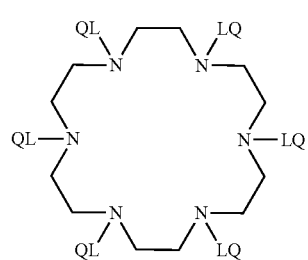
(D3)
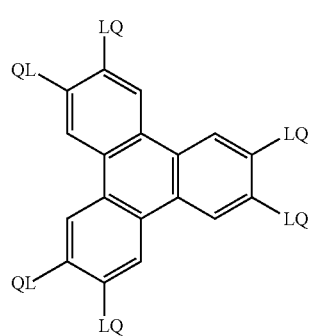
(D4)
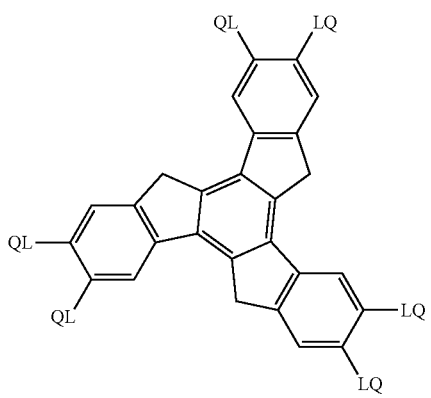
(D5)
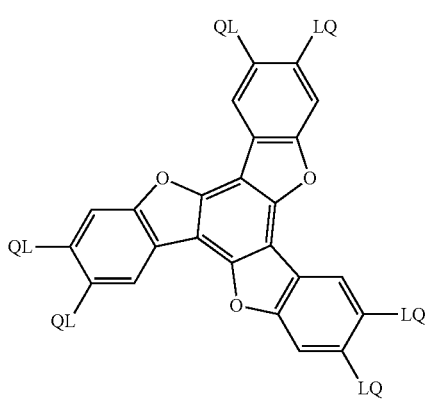
(D6)
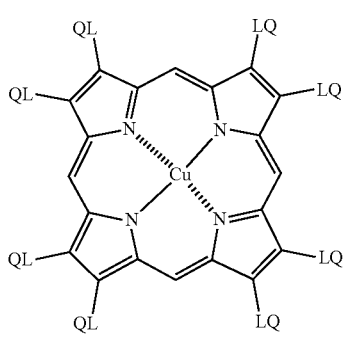
(D7)
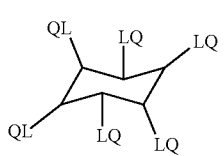
(D8)

-continued
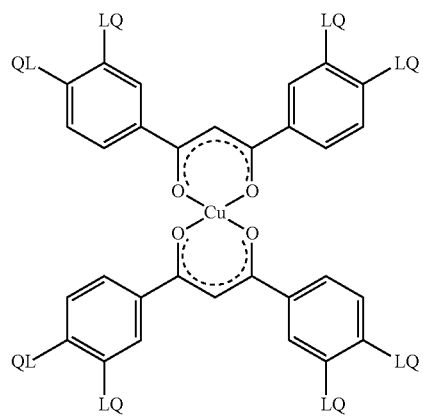
(D9)
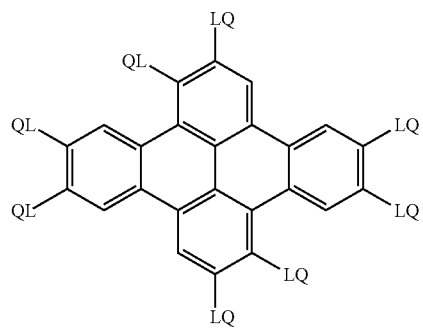
(D10)
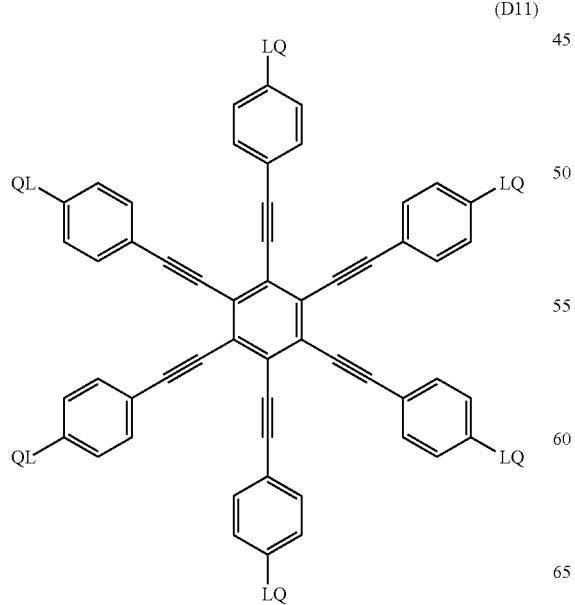
(D11)
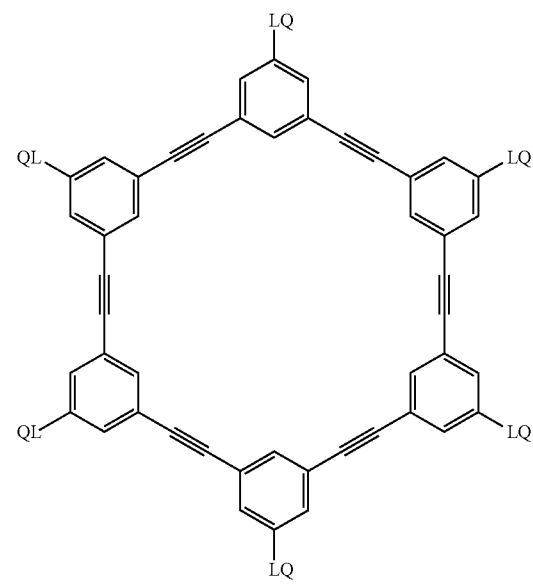
(D12)
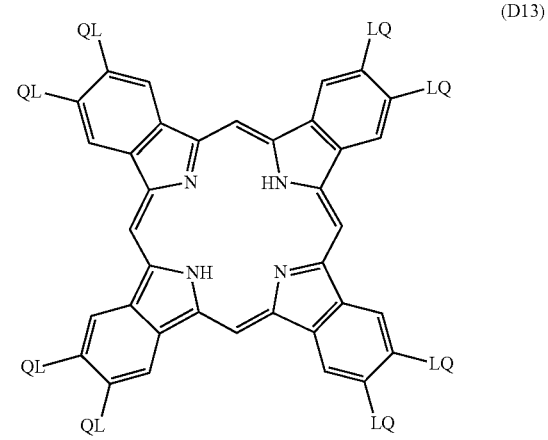
(D13)
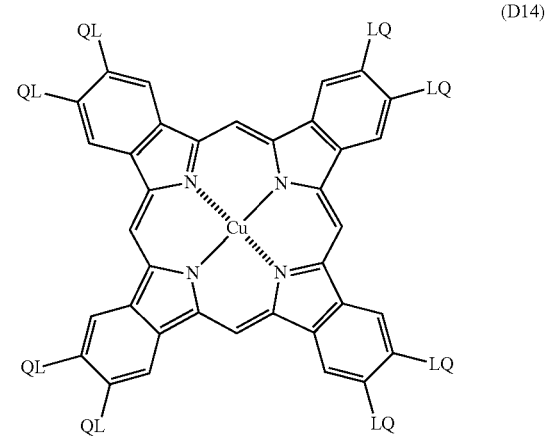
(D14)

-continued

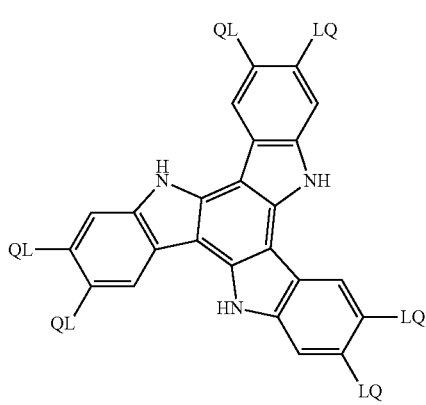
(D15)

In Formulae (D1) to (D15), L represents a divalent linking group.

The divalent linking group represented by L has the same definition as the divalent linking group represented by $L^{c1}$ in Formula (1), and suitable aspects thereof are also the same.

Particularly, from the viewpoint of further improving the thermal conductivity of the thermally conductive material, L's preferably each independently represent a group selected from the group consisting of an alkylene group, an alkenylene group, an arylene group, —C(=O)—, —NH—, —O—, —S—, and a combination of these, and more preferably each independently represent a group obtained by combining two or more groups selected from the group consisting of an alkylene group, an alkenylene group, an arylene group, —C(=O)—, —NH—, —O—, and —S—.

The number of carbon atoms in the alkylene group is preferably 1 to 12. The number of carbon atoms in the alkenylene group is preferably 2 to 12. The number of carbon atoms in the arylene group is preferably equal to or smaller than 10.

The alkylene group, the alkenylene group, and the arylene group may have a substituent (preferably an alkyl group, a halogen atom, cyano, an alkoxy group, an acyloxy group, and the like).

Examples of L will be shown below. In the following examples, the bond on the left side is bonded to the central structure of a compound represented by any of Formulae (D1) to (D15) (hereinafter, simply referred to as "central ring" as well), and the bond on the right side is bonded to Q.

AL means an alkylene group or an alkenylene group, and AR means an arylene group.

From the viewpoint of further improving the thermal conductivity of the thermally conductive material by causing the disk-like compound to express liquid crystallinity, in the compound represented by Formula (D4), L preferably represents a divalent linking group having a partial structure represented by *¹-alkylene group-O—C(=O)—*², *¹-alkylene group-C(=O)—O-*², *¹—O—C(=O)-alkylene group-*², *¹—C(=O)—O-alkylene group-*², *¹-C(=O)—O-arylene group-O-*², or *¹—O—C(=O)-arylene group-O-*². *¹ represents a position of binding to the central ring, and *² represents the other binding position. The other binding position represented by *² represents a position of binding to another atom in L or a position of binding to Q.

For example, L101 shown below corresponds to a divalent linking group having a partial structure represented by *¹-alkylene group-C(=O)—O-*².

L101: -AL-C(=O)—O-AL-
L102: -AL-C(=O)—O-AL-O—
L103: -AL-C(=O)—O-AL-O-AL-
L104: -AL-C(=O)—O-AL-O—C(=O)—
L105: —C(=O)-AR—O-AL-
L106: —C(=O)-AR—O-AL-O—
L107: —C(=O)-AR—O-AL-O—C(=O)—
L108: —C(=O)—NH-AL-
L109: —NH-AL-O—
L110: —NH-AL-O—C(=O)—
L111: —O-AL-
L112: —O-AL-O—
L113: —O-AL-O—C(=O)—
L114: —O-AL-O—C(=O)—NH-AL-
L115: —O-AL-S-AL-
L116: —O—C(=O)-AL-AR—O-AL-O—C(=O)—
L117: —O—C(=O)-AR—O-AL-C(=O)—
L118: —O—C(=O)-AR—O-AL-O—C(=O)—
L119: —O—C(=O)-AR—O-AL-O-AL-O—C(=O)—
L120: —O—C(=O)-AR—O-AL-O-AL-O-AL-O—C(=O)—
L121: —S-AL-
L122: —S-AL-O—
L123: —S-AL-O—C(=O)—
L124: —S-AL-S-AL-
L125: —S-AR-AL-
L126: —O—C(=O)-AL-
L127: —O—C(=O)-AL-O—
L128: —O—C(=O)-AR—O-AL-
L129: —O—C(=O)—
L130: —O—C(=O)-AR—O-AL-O—C(=O)-AL-S-AR—
L131: —O—C(=O)-AL-S-AR—
L132: —O—C(=O)-AR—O-AL-O—C(=O)-AL-S-AL-
L133: —O—C(=O)-AL-S-AR—
L134: —O-AL-S-AR—
L135: -AL-C(=O)—O-AL-O—C(=O)-AL-S-AR—
L136: -AL-C(=O)—O-AL-O—C(=O)-AL-S-AL-
L137: —O-AL-O-AR—
L138: —O-AL-O—C(=O)-AR—
L139: —O-AL-NH-AR—
L140: —O—C(=O)-AL-O-AR—
L141: —O—C(=O)-AR—O-AL-O-AR—
L142: -AL-C(=O)—O-AR—
L143: -AL-C(=O)—O-AL-O-AR—

In Formulae (D1) to (D15), Q represents a hydrogen atom or a substituent. Q has the same definition as Q described above. Here, one or more Q's represents the reactive functional group described above. Particularly, from the viewpoint of further improving the thermal conductivity of the thermally conductive material, it is preferable that all the Q's represent the reactive functional group.

Among the compounds represented by Formulae (D1) to (D15), from the viewpoint of further improving the thermal conductivity of the thermally conductive material, the compound represented by Formula (D4) is preferable. In other words, it is preferable that the specific disk-like compound has a triphenylene ring as the central ring.

As the compound represented by Formula (D4), from the viewpoint of further improving the thermal conductivity of the thermally conductive material, a compound represented by Formula (XI) is preferable.

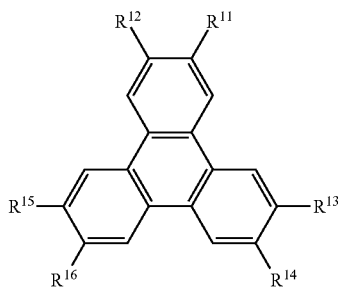

Formula (XI)

In Formula (XI), $R^{11}$, $R^{12}$, $R^{13}$, $R^{14}$, $R^{15}$, and $R^{16}$ each independently represent *—$X^{11}$-$L^{11}$-$P^{11}$ or *—$X^{12}$-$L^{12}$-$Y^{12}$.

* represents a position of binding to a triphenylene ring.

Among $R^{11}$, $R^2$, $R^{13}$, $R^{14}$, $R^{15}$, and $R^{16}$, two or more groups represent *—$X^{11}$-$L^{11}$-$P^{11}$. It is preferable that 3 or more groups among $R^{11}$, $R^{12}$, $R^{13}$, $R^{14}$, $R^{15}$, and $R^{16}$ represent *—$X^{11}$-$L^{11}$-$P^{11}$.

Particularly, from the viewpoint of further improving the thermal conductivity of the thermally conductive material, it is preferable that one or more groups between $R^{11}$ and $R^{12}$, one or more groups between $R^{13}$ and $R^{14}$, and one or more groups between $R^{15}$ and $R^{16}$ represent *—$X^{11}$-$L^{11}$-$P^{11}$.

It is more preferable that all of the $R^{11}$, $R^{12}$, $R^{13}$, $R^{14}$, $R^{15}$, and $R^{16}$ represent *—$X^{11}$-$L^{11}$-$P^{11}$. In addition, it is even more preferable that all of the $R^{11}$, $R^{12}$, $R^{13}$, $R^{14}$, $R^{15}$, and $R^{16}$ are the same as each other.

$X^{11}$'s each independently represent a single bond, —O—, —C(=O)—, —NH—, —OC(=O)—, —OC(=O)O—, —OC(=O)NH—, —OC(=O)S—, —C(=O)O—, —C(=O)NH—, —C(=O)S—, —NHC(=O)—, —NHC(=O)O—, —NHC(=O)NH—, —NHC(=O)S—, —S—, —SC(=O)—, —SC(=O)O—, —SC(=O)NH—, or —SC(=O)S—.

Particularly, $X^{11}$'s preferably each independently represent —O—, —OC(=O)—, —OC(=O)O—, —OC(=O)NH—, —C(=O)O—, —C(=O)NH—, —NHC(=O)—, or —NHC(=O)O—, more preferably each independently represent —O—, —OC(=O)—, —C(=O)O—, —OC(=O)NH—, or —C(=O)NH—, and even more preferably each independently represent —C(=O)O—.

$L^{11}$'s each independently represent a single bond or a divalent linking group.

Examples of the divalent linking group include —O—, —OC(=O)—, —C(=O)O—, —S—, —NH—, an alkylene group (preferably having 1 to 10 carbon atoms, more preferably having 1 to 8 carbon atoms, and even more preferably having 1 to 7 carbon atoms), an arylene group (preferably having 6 to 20, more preferably having 6 to 14 carbon atoms, and even more preferably having 6 to 10 carbon atoms), and a group obtained by combining these.

Examples of the alkylene group include a methylene group, an ethylene group, a propylene group, a butylene group, a pentylene group, a hexylene group, and a heptylene group.

Examples of the arylene group include a 1,4-phenylene group, a 1,3-phenylene group, a 1,4-naphthylene group, a 1,5-naphthylene group, and an anthracenylene group. Among these, a 1,4-phenylene group is preferable.

Each of the alkylene group and the arylene group may have a substituent. The number of substituents is preferably 1 to 3, and more preferably 1. The substitution position of the substituent is not particularly limited. As the substituent, a halogen atom or an alkyl group having 1 to 3 carbon atoms is preferable, and a methyl group is more preferable.

It is also preferable that the alkylene group and the arylene group are unsubstituted. Particularly, it is preferable that the alkylene group is unsubstituted.

Examples of —$X^{11}$-$L^{11}$ include L101 to L143 that are examples of L described above.

From the viewpoint of further improving the thermal conductivity of the thermally conductive material by causing the disk-like compound to express liquid crystallinity, —$X^{11}$-$L^{11}$- preferably represents a divalent linking group having a partial structure represented by *¹—O—C(=O)-alkylene group-*², *¹-C(=O)—O-alkylene group-*², *¹-C(=O)—O-arylene group-O—*², or *¹—O—C(=O)-arylene group-O—*². *¹ represents a position of binding to a triphenylene ring. *² represents the other binding position. The other binding position represented by *² represents a position of binding to another atom in $L^{11}$ or a position of binding to $P^{11}$.

$P^{11}$'s each independently represent a hydroxyl group, a carboxylic acid group, a carboxylic acid anhydride group, an amino group, or a cyanate ester group. Particularly, from the viewpoint of further improving thermal conductivity, $P^{11}$'s preferably each independently represent a hydroxyl group, a carboxylic acid group, or a carboxylic acid anhydride group.

In a case where $P^{11}$ represents a hydroxyl group, $L^{11}$ contains an arylene group, and it is preferable that the arylene group is bonded to $P^{11}$.

$X^{12}$ is the same as $X^{11}$, and suitable conditions thereof are also the same.

$L^{12}$ is the same as $L^{11}$, and suitable conditions thereof are also the same.

Examples of —$X^{12}$-$L^{12}$- include L101 to L143 that are examples of L described above.

From the viewpoint of further improving the thermal conductivity of the thermally conductive material by causing the disk-like compound to express liquid crystallinity, —$X^{12}$-$L^{12}$- preferably represents a divalent linking group having a partial structure represented by *¹—O—C(=O)-alkylene group-*², *¹-C(=O)—O-alkylene group-*², *¹-C(=O)—O-arylene group-*², or *¹—O—C(=O)-arylene group-*². *¹ represents a position of binding to a triphenylene ring. *² represents the other binding position. The other binding position represented by *² represents a position of binding to another atom in $L^{12}$ or a position of binding to $Y^{12}$.

$Y^{12}$ represents a hydrogen atom, a linear, branched, or cyclic alkyl group having 1 to 20 carbon atoms, or a group obtained in a case where one, two, or more methylene groups in a linear, branched, or cyclic alkyl group having 1 to 20 carbon atoms are substituted with —O—, —S—, —NH—, —N(CH₃)—, —C(=O)—, —OC(=O)—, or —C(=O)O—.

Provided that $Y^{12}$ represents a linear, branched, or cyclic alkyl group having 1 to 20 carbon atoms or a group obtained in a case where one, two, or more methylene groups in a linear, branched, or cyclic alkyl group having 1 to 20 carbon atoms are substituted with —O—, —S—, —NH—, —N(CH₃)—, —C(=O)—, —OC(=O)—, or —C(=O)O—, one or more hydrogen atoms contained in $Y^{12}$ may be substituted with a halogen atom.

$Y^{12}$ is preferably a hydrogen atom, a linear, branched, or cyclic alkyl group having 1 to 20 carbon atoms, or an alkylene oxide group having 1 to 20 carbon atoms, and more preferably a linear or branched alkyl group having 1 to 12 carbon atoms or an ethylene oxide group or a propylene oxide group having 1 to 20 carbon atoms.

Regarding specific examples of the compound represented by Formula (XI), it is possible to refer to the compounds described in paragraphs "0028" to "0036" in JP1995-281028A (JP-H07-281028A), JP1995-306317A (JP-H07-306317A), paragraphs "0016" to "0018" in JP2005-156822A, paragraphs "0067" to "0072" in JP2006-301614A, Liquid Crystal Handbook (published on 2000 from MARUZEN Co., Ltd.), pp. 330-333.

The compound represented by Formula (XI) can be synthesized based on the methods described in JP1995-306317A (JP-H07-306317A), JP1995-281028A (JP-H07-281028A), JP2005-156822A, and JP2006-301614A.

Next, the compound represented by Formula (D16) will be specifically described.

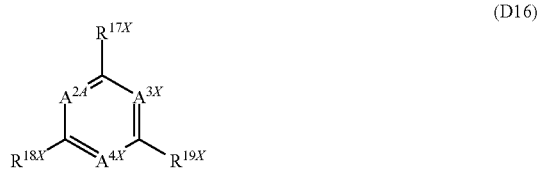

(D16)

In Formula (D16), $A^{2X}$, $A^{3X}$, and $A^{4X}$ each independently represent —CH= or —N=. Particularly, $A^{2X}$, $A^{3X}$, and $A^{4X}$ preferably each independently represent —CH=.

$R^{17X}$, $R^{18X}$, and $R^{19X}$ each independently represent *—$X^{211X}$—$(Z^{21X}$—$X^{212X})_{n21X}$-$L^{21X}$-Q. * represents a position of binding to the central ring.

$X^{211X}$ and $X^{212X}$ each independently represent a single bond, —O—, —C(=O)—, —NH—, —OC(=O)—, —OC(=O)O—, —OC(=O)NH—, —OC(=O)S—, —C(=O)O—, —C(=O)NH—, —C(=O)S—, —NHC(=O)—, —NHC(=O)O—, —NHC(=O)NH—, —NHC(=O)S—, —S—, —SC(=O)—, —SC(=O)O—, —SC(=O)NH—, or —SC(=O)S—.

$Z^{21X}$'s each independently represent a 5-membered or 6-membered aromatic ring group or a 5-membered or 6-membered non-aromatic ring group.

$L^{21X}$ represents a single bond or a divalent linking group.

Q has the same definition as Q in Formulae (D1) to (D15), and preferred conditions thereof are also the same. That is, at least one Q among a plurality of Q's represents a hydroxyl group, a carboxylic acid group, a carboxylic acid anhydride group, an amino group, or a cyanate ester group.

n21X represents an integer of 0 to 3. In a case where n21X is equal to or greater than 2, a plurality of groups represented by ($Z^{21X}$—$X^{212X}$) may be the same as or different from each other.

As the compound represented by Formula (D16), a compound represented by Formula (XII) is preferable.

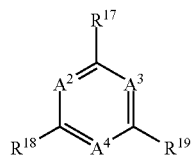

(XII)

In Formula (XII), $A^2$, $A^3$, and $A^4$ each independently represent —CH= or —N=. Particularly, $A^2$, $A^3$, and $A^4$ preferably represent —CH=. In other words, it is also preferable that the specific disk-like compound has a benzene ring as the central ring.

$R^{17}$, $R^{18}$, and $R^{19}$ each independently represent *—$X^{211}$—$(Z^{21}$—$X^{212})_{n21}$-$L^{21}$-$P^{21}$ or *—$X^{221}$—$(Z^{22}$—$X^{222})_{n22}$—$Y^{22}$. * represents a position of binding to the central ring.

Two or more groups among $R^{17}$, $R^{18}$, and $R^{19}$ represent *—$X^{211}$—$(Z^{21}$—$X^{212})_{n21}$-$L^{21}$-$P^{21}$. From the viewpoint of further improving the thermal conductivity of the thermally conductive material, it is preferable that all of the $R^{17}$, $R^{18}$, and $R^{19}$ represent *—$X^{211}$—$(Z^{21}$—$X^{212})_{n21}$-$L^{21}$-$P^{21}$.

In addition, it is preferable that all of the $R^{17}$, $R^{18}$, and $R^{19}$ are the same as each other.

$X^{211}$, $X^{212}$, $X^{221}$, and $X^{222}$ each independently represent a single bond, —O—, —C(=O)—, —NH—, —OC(=O)—, —OC(=O)O—, —OC(=O)NH—, —OC(=O)S—, —C(=O)O—, —C(=O)NH—, —C(=O)S—, —NHC(=O)—, —NHC(=O)O—, —NHC(=O)NH—, —NHC(=O)S—, —S—, —SC(=O)—, —SC(=O)O—, —SC(=O)NH—, or —SC(=O)S—.

Particularly, it is preferable that $X^{211}$, $X^{212}$, $X^{221}$, and $X^{222}$ each independently represent a single bond, —O—, —C(=O)O—, or —OC(=O)—.

$Z^{21}$ and $Z^{22}$ each independently represent a 5-membered or 6-membered aromatic ring group or a 5-membered or 6-membered non-aromatic ring group. Examples thereof include a 1,4-phenylene group, a 1,3-phenylene group, and an aromatic heterocyclic group.

The aromatic ring group and the non-aromatic ring group may have a substituent. The number of substituents is preferably 1 or 2, and more preferably 1. The substitution position of the substituent is not particularly limited. As the substituent, a halogen atom or a methyl group is preferable. It is also preferable that the aromatic ring group and the non-aromatic ring group are unsubstituted.

Examples of the aromatic heterocyclic group include the following aromatic heterocyclic groups.

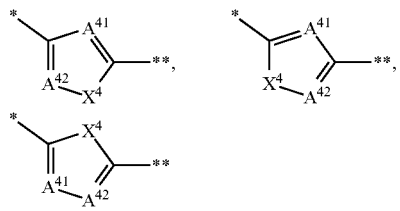

In the formulae, * represents a moiety bonded to $X^{211}$ or $X^{221}$. ** represents a moiety bonded to $X^{212}$ or $X^{222}$. $A^{41}$ and $A^{42}$ each independently represent a methine group or a nitrogen atom. $X^4$ represents an oxygen atom, a sulfur atom, a methylene group, or an imino group.

It is preferable that at least one of $A^{41}$ or $A^{42}$ is a nitrogen atom. It is more preferable that both the $A^{41}$ and $A^{42}$ are nitrogen atoms. Furthermore, it is preferable that $X^4$ is an oxygen atom.

In a case where n21 and n22, which will be described later, are equal to or greater than 2, a plurality of groups represented by ($Z^{21}$—$X^{212}$) and ($Z^{22}$—$X^{222}$) may be the same as or different from each other.

$L^{21}$'s each independently represent a single bond or a divalent linking group, and has the same definition as $L^{11}$ in Formula (XI) described above. $L^{21}$ is preferably —O—, —OC(=O)—, —C(=O)O—, —S—, —NH—, an alkylene group (preferably having 1 to 10 carbon atoms, more preferably having 1 to 8 carbon atoms, and even more preferably having 1 to 7 carbon atoms), an arylene group (preferably having 6 to 20 carbon atoms, more preferably having 6 to 14 carbon atoms, and even more preferably having 6 to 10 carbon atoms), or a group obtained by combining these.

In a case where n22, which will be described later, is equal to or greater than 1, examples of —$X^{212}$-$L^{21}$- include L101 to L143 that are examples of L in Formulae (D1) to (D15) described above.

$P^{21}$'s each independently represent a hydroxyl group, a carboxylic acid group, a carboxylic acid anhydride group, an amino group, or a cyanate ester group. Particularly, from the viewpoint of further improving the thermal conductivity of the thermally conductive material, $P^{21}$'s preferably each independently represent a hydroxyl group, a carboxylic acid group, or a carboxylic acid anhydride group.

$Y^{22}$'s each independently represent a hydrogen atom, a linear, branched, or cyclic alkyl group having 1 to 20 carbon atoms, or a group obtained in a case where one, two, or more methylene groups in a linear, branched, or cyclic alkyl group having 1 to 20 carbon atoms are substituted with —O—, —S—, —NH—, —N(CH$_3$)—, —C(=O)—, —OC(=O)—, or —C(=O)O—. $Y^{22}$ has the same definition as $Y^{12}$ in Formula (XI), and preferred ranges thereof are also the same.

n21 and n22 each independently represent an integer of 0 to 3. From the viewpoint of further improving thermal conductivity, each of n21 and n22 is preferably an integer of 1 to 3, and more preferably 2 or 3.

As the compound represented by Formula (XII), for example, the following compounds are preferable. In the following structural formulae, R represents —$X^{212}$-$L^{21}$-$P^{21}$

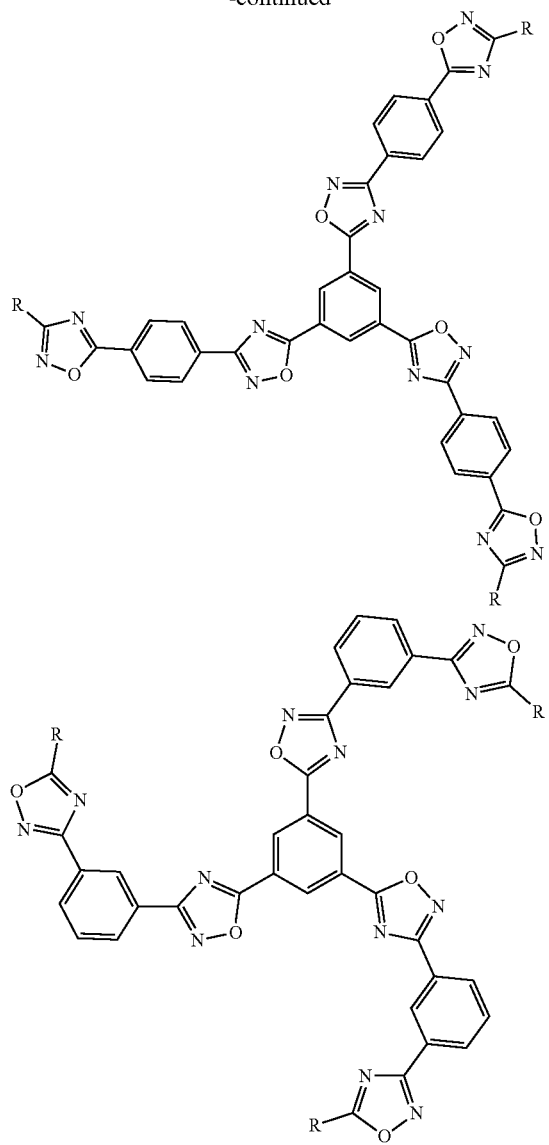

-continued

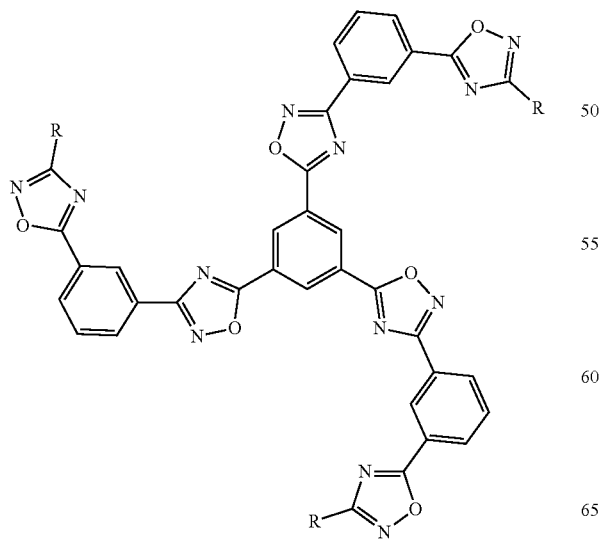

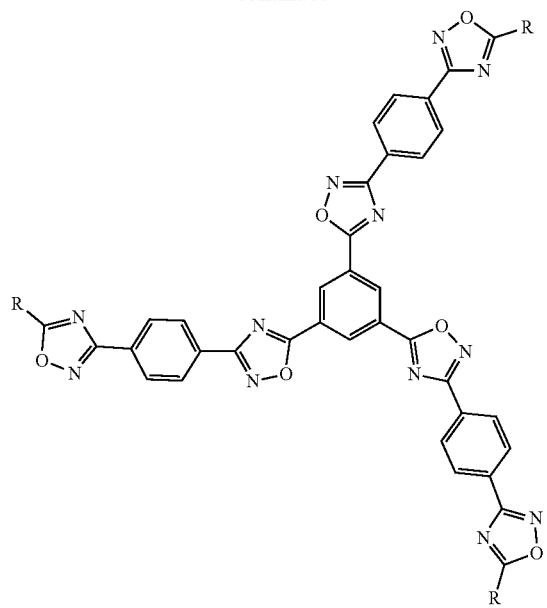

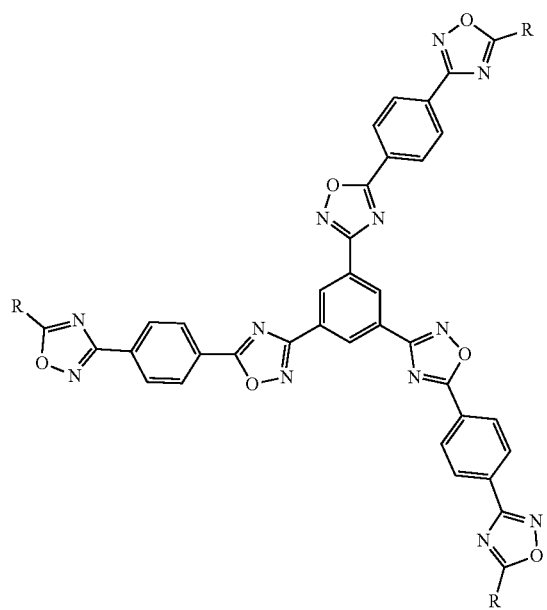

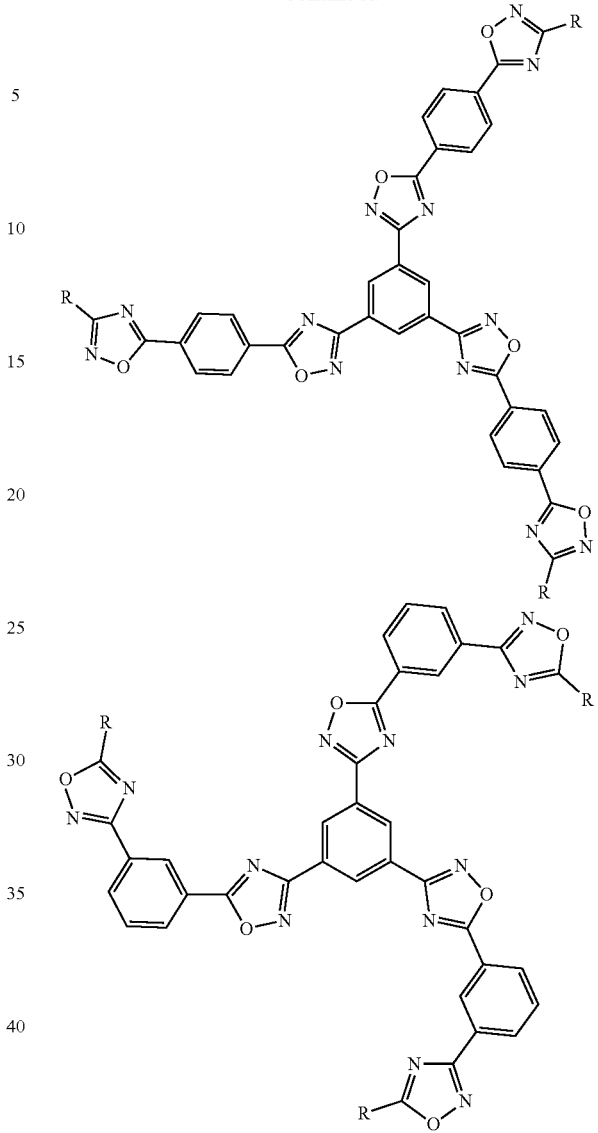

Regarding the details and specific examples of the compound represented by Formula (XII), the description in paragraphs "0013" to "0077" in JP2010-244038A can be referred to. What is described in the paragraphs is incorporated into the present specification. The compound represented by Formula (XII) can be synthesized based on the methods described in JP2010-244038A, JP2006-076992A, and JP2007-00220A. From the viewpoint of reinforcing stacking by reducing electron density such that a columnar bundle is easily formed, the specific disk-like compound is preferable a compound having a hydrogen bonding functional group. Examples of the hydrogen bonding functional group include —OC(=O)NH—, —C(=O)NH—, —NHC (=O)—, —NHC(=O)O—, —NHC(=O)NH—, —NHC (=O)S—, —SC(=O)NH—, and the like.

One kind of specific disk-like compound may be used singly, or two or more kinds of specific disk-like compounds may be used in combination.

[Crosslinking Compound]

The crosslinking compound is a compound reacting with the specific disk-like compound described above.

The crosslinking compound has a group reacting with the reactive functional group (hereinafter, referred to as "crosslinking group" as well).

Examples of the crosslinking group include an oxiranyl group, an oxetanyl group, a hydroxyl group, a carboxylic acid group, a halogenated benzyl group, a carboxylic acid anhydride group, a cyanate ester group, an isocyanate group, an amino group, an aldehyde group, an aziridine group, and an alkoxysilyl group.

The crosslinking group is appropriately selected according to the type of the reactive functional group.

Examples of the crosslinking group usable in a case where the reactive functional group is a hydroxyl group include an oxiranyl group, an oxetanyl group, a carboxylic acid group, a halogenated benzyl group, a carboxylic acid anhydride group, an isocyanate group, and an alkoxysilyl group.

Examples of the crosslinking group usable in a case where the reactive functional group is a carboxylic acid group include an oxiranyl group, an oxetanyl group, a halogenated benzyl group, a cyanate ester group, an amino group, an isocyanate group, and an aziridine group.

Examples of the crosslinking group usable in a case where the reactive functional group is a carboxylic acid anhydride group include an oxiranyl group, an oxetanyl group, and a hydroxyl group.

Examples of the crosslinking group usable in a case where the reactive functional group is an amino group include an oxiranyl group, an oxetanyl group, a halogenated benzyl group, an isocyanate group, an aldehyde group, and a carbonyl group.

Examples of the crosslinking group usable in a case where the reactive functional group is a cyanate ester group include an oxiranyl group, a carboxylic acid group, and an unsaturated polymerizable group.

Examples of the crosslinking group usable in a case where the reactive functional group is a thiol group include an oxiranyl group, an oxetanyl group, a halogenated benzyl group, a carboxylic acid anhydride group, an isocyanate group, and an alkoxysilyl group.

Particularly, from the viewpoint of further improving the thermal conductivity of the thermally conductive material and from the viewpoint of improving the adhesiveness of the thermally conductive material with respect to devices and the like, the crosslinking group is preferably an oxiranyl group or an oxetanyl group, and more preferably an oxiranyl group.

In the present specification, the oxiranyl group is a functional group which is referred to as epoxy group as well. The oxiranyl group may be a group containing oxacyclopropane (oxirane). For example, the oxiranyl group contains a group, in which 2 adjacent carbon atoms in a saturated hydrocarbon ring group form an oxirane ring by being bonded to each other through an oxo group (—O—), and the like.

Hereinafter, a crosslinking compound having an oxiranyl group (epoxy group) as a crosslinking group will be referred to as epoxy compound as well.

The number of crosslinking groups that the crosslinking compound has is not particularly limited, but is preferably 2 to 8 and more preferably 2 to 6.

The crosslinking compound is particularly preferably an epoxy compound.

Examples of the epoxy compound include a rod-like compound having an epoxy group (rod-like epoxy compound) represented by an epoxy compound represented by Formula (E1) which will be described later, a bisphenol A diglycidyl ether resin, or a bisphenol F diglycidyl ether resin and a disk-like compound having an epoxy group (disk-like epoxy compound).

The definition of the disk-like compound is as described above.

As the crosslinking compound, from the viewpoint of further improving the thermal conductivity of the thermally conductive material, the epoxy compound represented by Formula (E1) which will be described later or the disk-like epoxy compound is preferable.

The crosslinking compound may or may not have liquid crystallinity. From the viewpoint of further improving the thermal conductivity of the thermally conductive material, it is preferable that the crosslinking compound has liquid crystallinity.

Hereinafter, each of the rod-like epoxy compound and the disk-like epoxy compound will be specifically described.

(Rod-Like Epoxy Compound)

In a case where the crosslinking compound is a rod-like epoxy compound, the number of epoxy groups that the rod-like epoxy compound has is not particularly limited, but is preferably 2 to 8, more preferably 2 to 6, and even more preferably 2.

As the rod-like epoxy compound, particularly, from the viewpoint of further improving the thermal conductivity of the thermally conductive material, the epoxy compound represented by Formula (E1) is more preferable.

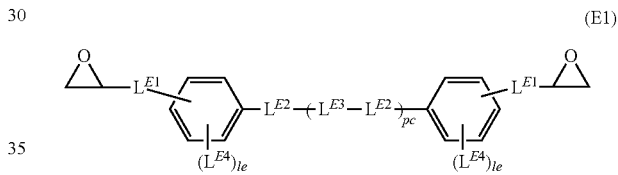

(E1)

In Formula (E1), $L^{E1}$'s each independently represent a single bond or a divalent linking group.

$L^{E1}$ is particularly preferably a divalent linking group.

As the divalent linking group, —O—, —S—, —C(=O)—, —NH—, —CH=CH—, —C≡C—, —CH=N—, —N=CH—, —N=N—, an alkylene group which may have a substituent, or a group obtained by combining two or more groups among the above is preferable, and —O-alkylene group- or -alkylene group-O— is more preferable.

The alkylene group may be any of a linear, branched, or cyclic alkylene group. As the alkylene group, a linear alkylene group having 1 or 2 carbon atoms is preferable.

$L^{E2}$'s each independently represent a single bond, —CH=CH—, —C(=O)—O—, —O—C(=O)—, —C(—CH$_3$)=CH—, —CH=C(—CH$_3$)—, —CH=N—, —N=CH—, —N=N—, —C≡C—, —N=N$^+$(—O—)—, —N$^+$(—O—)=N—, —CH=N$^+$(—O—)—, —N$^+$(—O$^-$—)=CH—, —CH=CH—C(=O)—, —C(=O)—CH=CH—, —CH=C(—CN)—, or —C(—CN)=CH—.

Particularly, $L^{E2}$'s preferably each independently represent a single bond, —C(=O)—O— or —O—C(=O)—.

$L^{E3}$'s each independently represent a single bond, a 5-membered or 6-membered aromatic ring group which may have a substituent, a 5-membered or 6-membered non-aromatic ring group which may have a substituent, or a polycyclic group formed of these rings.

Examples of the aromatic ring group and the non-aromatic ring group represented by $L^{E3}$ include a 1,4-cyclohexanediyl group, a 1,4-cyclohexanediyl group, a 1,4-phenylene group, a pyrimidine-2,5-diyl group, a pyridine-2,5-diyl group, a 1,3,4-thiadiazole-2,5-diyl group, a 1,3,4-oxadiazole-2,5-diyl group, a naphthalene-2,6-diyl group, a naphthalene-1,5-diyl group, a thiophene-2,5-diyl group, and a pyridazine-3,6-diyl group which may have a substituent. In a case where $L^{E3}$ is a 1,4-cyclohexanediyl group, $L^{E3}$ may be a structural isomer of a trans isomer or a structural isomer of a cis isomer or may be a mixture of these isomers at any ratio. Particularly, $L^{E3}$ is preferably a trans isomer.

Particularly, $L^{E3}$ is preferably a single bond, a 1,4-phenylene group, or a 1,4-cyclohexanediyl group.

As each of the substituents that the group represented by $L^{E3}$ has, an alkyl group, an alkoxy group, a halogen atom, a cyano group, a nitro group, or an acetyl group is preferable, and an alkyl group (preferably having 1 carbon atom) is more preferable.

In a case where $L^{E3}$ has a plurality of substituents, the substituents may be the same as or different from each other.

pe represents an integer equal to or greater than 0.

In a case where pe is an integer equal to or greater than 2, a plurality of groups represented by (-$L^{E3}$-$L^{E2}$-) may be the same as or different from each other.

Particularly, pe is preferably 0 to 2, and more preferably 0 or 1.

L's each independently represent a substituent.

As each of the substituents, an alkyl group, an alkoxy group, a halogen atom, a cyano group, a nitro group, or an acetyl group is preferable, and an alkyl group (preferably having 1 carbon atom) is more preferable.

In a case where le, which will be described below, is an integer equal to or greater than 2, a plurality of $L^{E4}$'s in $(L^{E4})_{le}$ may be the same as or different from each other.

le's each independently represent an integer of 0 to 4.

Particularly, le's preferably each independently represent 0 to 2.

From the viewpoint of further improving thermal conductivity, the molecular weight of the epoxy compound represented by Formula (E1) is preferably 100 to 3,000, more preferably 200 to 2,500, and even more preferably 250 to 2,000.

One kind of epoxy compound represented by Formula (E1) may be used singly, or two or more kinds of epoxy compounds represented by Formula (E1) may be used in combination.

(Disk-Like Epoxy Compound)

The disk-like epoxy compound is not particularly limited as long as it is a disk-like compound having an epoxy group.

From the viewpoint of further improving the thermal conductivity of the thermally conductive material, the disk-like epoxy compound preferably has 3 to 8 epoxy groups, and more preferably has 3 to 6 epoxy groups.

A cured substance of a disk-like compound having 3 or more epoxy groups has a high glass transition temperature and exhibits excellent heat resistance.

Specific examples of the disk-like compound are not particularly limited, and include a compound having the aforementioned disk-like core portion as a partial structure.

One kind of crosslinking compound may be used singly, or two or more kinds of crosslinking compounds may be used in combination.

In the thermally conductive material according to the embodiment of the present invention, the content of the cured substance of the specific disk-like compound and the crosslinking compound with respect to the total mass of the thermally conductive material according to the embodiment of the present invention is preferably 5% to 95% by mass, more preferably 10% to 90% by mass, and even more preferably 15% to 80% by mass.

It is preferable that the cured substance of the specific disk-like compound and the crosslinking compound forms a columnar structure. The columnar structure has a high order parameter. Therefore, in a case where the cured substance forms the columnar structure, the thermal conductivity of the cured substance is further improved. In a case where the cured substance is measured by X-ray diffractometry (XRD), and a peak resulting from a columnar structure can be checked in a range equal to or smaller than $2\theta=10°$, the cured substance is regarded as forming a columnar structure.

The method for manufacturing the cured substance is not particularly limited, and examples thereof include a method of reacting the specific disk-like compound and the crosslinking compound with each other under the heating conditions described in <Method for curing composition> which will be described later.

[Other Components]

The thermally conductive material according to the embodiment of the present invention may contain other components in addition to the cured substance of the specific disk-like compound and the crosslinking compound.

The thermally conductive material may contain a non-cured specific disk-like compound and a non-cured crosslinking compound.

Typically, examples of those other components include an inorganic substance.

<Inorganic Substance>

From the viewpoint of further improving the thermal conductivity of the thermally conductive material, it is preferable that the thermally conductive material according to the embodiment of the present invention contains an inorganic substance.

As the inorganic substance, any of the inorganic substances that have been conventionally used as inorganic fillers for thermally conductive materials may be used. As the inorganic substance, an inorganic oxide or an inorganic nitride is preferable. The inorganic substance may be an inorganic oxynitride as well. The shape of the inorganic substance is not particularly limited. The inorganic substance may be in the form of particles, a film, or a plate. The inorganic substance in the form of particles has, for example, a rice grain shape, a spherical shape, a cubical shape, a spindle shape, a scale shape, an aggregated shape, or an amorphous shape.

Examples of the inorganic oxide include zirconium oxide ($ZrO_2$), titanium oxide ($TiO_2$), silicon oxide ($SiO_2$), aluminum oxide ($Al_2O_3$), iron oxide ($Fe_2O_3$, FeO, or $Fe_3O_4$), copper oxide (CuO or $Cu_2O$), zinc oxide (ZnO), yttrium oxide ($Y_2O_3$), niobium oxide ($Nb_2O_5$), molybdenum oxide ($MoO_3$), indium oxide ($In_2O_3$ or $In_2O$), tin oxide ($SnO_2$), tantalum oxide ($Ta_2O_5$), tungsten oxide ($WO_3$ or $W_2O_5$), lead oxide (PbO or $PbO_2$), bismuth oxide ($Bi_2O_3$), cerium oxide ($CeO_2$ or $Ce_2O_3$), antimony oxide ($Sb_2O_3$ or $Sb_2O_5$), germanium oxide ($GeO_2$ or GeO), lanthanum oxide ($La_2O_3$), and ruthenium oxide ($RuO_2$).

One kind of each of the above inorganic oxides may be used singly, or two or more kinds of the inorganic oxides may be used in combination.

The inorganic oxide is preferably titanium oxide, aluminum oxide, or zinc oxide.

The inorganic oxide may be an oxide that is generated in a case where a metal prepared as a non-oxide is oxidized due to the environment or the like.

Examples of the inorganic nitride include boron nitride (BN), carbon nitride ($C_3N_4$), silicon nitride ($Si_3N_4$), gallium nitride (GaN), indium nitride (InN), aluminum nitride (AlN), chromium nitride ($Cr_2N$), copper nitride ($Cu_3N$), iron nitride ($Fe_4N$), iron nitride ($Fe_3N$), lanthanum nitride (LaN), lithium nitride ($Li_3N$), magnesium nitride ($Mg_3N_2$), molybdenum nitride ($Mo_2N$), niobium nitride (NbN), tantalum nitride (TaN), titanium nitride (TiN), tungsten nitride ($W_2N$), tungsten nitride ($WN_2$), yttrium nitride (YN), and zirconium nitride (ZrN).

One kind of each of the above inorganic nitrides may be used singly, or two or more kinds of the inorganic nitrides may be used in combination.

The inorganic nitride preferably contains aluminum atoms, boron atoms, or silicon atoms. The inorganic nitride is preferably aluminum nitride, boron nitride, or silicon nitride, more preferably aluminum nitride or boron nitride, and particularly preferably boron nitride.

The size of the inorganic substance is not particularly limited. However, in view of further improving the dispersibility of the inorganic substance, the average particle diameter of the inorganic substance is preferably equal to or smaller than 500 µm, more preferably equal to or smaller than 300 µm, and even more preferably equal to or smaller than 200 µm. The lower limit thereof is not particularly limited. However, in view of handleability, the lower limit is preferably equal to or greater than 10 nm, and more preferably equal to or greater than 100 nm.

The average particle diameter is measured, for example, by a method of randomly selecting 100 inorganic substances by using an electron microscope, measuring the particle diameter (major axis) of each of the inorganic substances, and calculating the arithmetic mean thereof. In a case where a commercial inorganic substance is used, the particle diameter described in the catalog may be used.

One kind of inorganic substance may be used singly, or two or more kinds of inorganic substances may be used in combination.

In the thermally conductive material according to the embodiment of the present invention, the content of the inorganic substance with respect to the total mass of the thermally conductive material according to the embodiment of the present invention is preferably 30% to 95% by mass, more preferably 35% to 90% by mass, and even more preferably 40% to 90% by mass.

The thermally conductive material may contain the cured substance described above, and the method for manufacturing the thermally conductive material is not particularly limited. However, it is preferable to form the thermally conductive material by using a composition for forming a thermally conductive material (present composition) containing a specific disk-like compound and a crosslinking compound. That is, it is preferable to obtain the thermally conductive material containing the cured substance by curing the composition described above.

Hereinafter, the present composition and the method for manufacturing the thermally conductive material according to the embodiment of the present invention by using the present composition will be described.

[Composition for Forming Thermally Conductive Material]

The present composition contains a specific disk-like compound and a crosslinking compound.

The definition of the specific disk-like compound and the crosslinking compound is as described above.

In the present composition, the content of the specific disk-like compound with respect to the total solid content in the composition is preferably 5% to 95% by mass, more preferably 10% to 90% by mass, and even more preferably 15% to 80% by mass.

In the present composition, the content of the crosslinking compound with respect to the total solid content in the composition is preferably 5% to 95% by mass, more preferably 10% to 90% by mass, and even more preferably 15% to 80% by mass.

Furthermore, the content of the crosslinking compound in the composition is set such that a ratio between the number of crosslinking groups that the crosslinking compound in the composition has and the number of reactive functional groups that the specific disk-like compound in the composition has (number of crosslinking groups/number of reactive functional groups) preferably becomes 0.1 to 10.0, more preferably becomes 0.1 to 9.0, and even more preferably becomes 0.1 to 8.0.

The present composition may contain other components such as an inorganic substance, a solvent, and a curing accelerator.

The definition of the inorganic substance is as described above.

<Solvent>

The present composition may further contain a solvent.

The type of the solvent is not particularly limited, but an organic solvent is preferred. Examples of the organic solvent include ethyl acetate, methyl ethyl ketone (MEK), dichloromethane, and tetrahydrofuran (THF).

The content of the solvent in the present composition is set such that the total mass of the total solid content (concentration of solid contents) in the present composition with respect to the total mass of the present composition preferably becomes 1% to 90% by mass, more preferably becomes 5% to 85% by mass, and even more preferably becomes 10% to 80% by mass.

<Curing Accelerator>

Examples of the curing accelerator include triphenylphosphine, 2-ethyl-4-methylimidazole, a boron trifluoride amine complex, 1-benzyl-2-methylimidazole, and the curing accelerator described in paragraph "0052" in JP2012-067225A. Among these, triphenylphosphine is preferable.

In the present composition, the content of the curing accelerator with respect to the total solid content in the composition is preferably 0.01% to 30% by mass, more preferably 0.01% to 20% by mass, and even more preferably 0.01% to 10% by mass.

The amount of the curing accelerator used with respect to the total mass of the specific disk-like compound and the crosslinking compound is preferably 0.01% to 30% by mass, more preferably 0.01% to 20% by mass, and even more preferably 0.01% to 10% by mass.

In a case where an epoxy compound is used as the crosslinking compound, and the specific disk-like compound has an amino group, sometimes it is preferable that a curing accelerator is not used. This is because the amino group is excellently reactive with an oxiranyl group (epoxy group), and accordingly, sometimes a curing accelerator does not need to be used to further improve reactivity.

In a case where the present composition contains the specific disk-like compound exhibiting liquid crystallinity, and the composition exhibits liquid crystallinity, the composition can be suitably used as a curable composition excellent in thermal conductivity and heat resistance. That is, it is preferable that the present composition has an aspect in which the composition contains a disk-like liquid crystal compound, which has one or more reactive functional groups selected from the group consisting of a hydroxyl group, a carboxylic acid group, a carboxylic acid anhydride group, an amino group, a cyanate ester group, and a thiol group, and a crosslinking compound, which has a group reacting with the reactive functional groups, so as to exhibit liquid crystallinity.

In a case where the present composition has the above aspect, it is preferable that the crosslinking compound also exhibits liquid crystallinity.

As the disk-like liquid crystal compound, a disk-like liquid crystal compound represented by Formula (1A), which will be described later, is preferable.

The crosslinking compound is as described above.

<Method for Manufacturing Composition>

As the method for manufacturing the present composition, known methods can be adopted without particular limitation. For example, the present composition can be manufactured by mixing together various components (the specific disk-like compound, the crosslinking compound, the inorganic substance, the curing accelerator, the solvent, and the like) described above by a known method. At the time of mixing, various components may be mixed together at once or sequentially mixed together.

<Method for Curing Composition>

As the method for curing the present composition, optimal methods are appropriately selected according to the type of the specific disk-like compound and the crosslinking compound without particular limitation. The curing method is not particularly limited, but is preferably a thermal curing reaction.

The heating temperature at the time of the thermal curing reaction is not particularly limited, and may be appropriately selected, for example, within a range of 50° C. to 250° C. At the time of performing the thermal curing reaction, a heating treatment may be performed plural times at different temperatures.

It is preferable that the present composition is subjected to a curing treatment after being made into a film or a sheet. Specifically, for example, the present composition may be subjected to a curing reaction after being made into a film by means of coating. At this time, press processing may be performed.

The curing treatment may be finished at a point in time when the present composition is in a semi-cured state. The thermally conductive material according to the embodiment of the present invention in a semi-cured state may be disposed so as to contact a device to be used or the like and may be further cured by means of heating and the like such that the thermally conductive material is permanently cured. It is also preferable that the device and the thermally conductive material according to the embodiment of the present invention may be bonded to each other by the heating and the like performed for permanently curing the thermally conductive material.

Regarding the preparation of the thermally conductive material including the curing reaction, "Highly Thermally Conductive Composite Material" (CMC Publishing CO., LTD., Yoshitaka Takezawa) can be referred to.

The shape of the thermally conductive material is not particularly limited, and the thermally conductive material can be molded in various shapes according to the use. Typically, the molded thermally conductive material has a sheet shape, for example.

Furthermore, it is preferable that the thermal conductivity of the thermally conductive material according to the embodiment of the present invention is not anisotropic but isotropic.

[Use of Thermally Conductive Material]

The thermally conductive material according to the embodiment of the present invention can be used as a heat dissipation material such as a heat dissipation sheet and used for dissipating heat from various devices. More specifically, in a case where a thermally conductive layer containing the thermally conductive material according to the embodiment of the present invention is disposed on a device so as to prepare a device with a thermally conductive layer, heat generated from the device can be efficiently dissipated by the thermally conductive layer.

The thermally conductive material according to the embodiment of the present invention has sufficient thermal conductivity and high heat resistance. Accordingly, the thermally conductive material is appropriate for dissipating heat from power semiconductor devices used in various electrical instruments such as personal computers, general home appliances, and automobiles.

Furthermore, the thermally conductive material according to the embodiment of the present invention has sufficient thermal conductivity even in a semi-cured state. Accordingly, the thermally conductive material can be used as a heat dissipation material disposed in portions to which light for photocuring does not easily reach, such as voids in members of various apparatuses. In addition, the thermally conductive material can also be used as an adhesive having thermal conductivity.

The thermally conductive material according to the embodiment of the present invention may be used in combination with other members in addition to the members formed of the present composition.

For example, the thermally conductive material in the form of a sheet may be combined with a support in the form of a sheet in addition to the layer formed of the present composition.

Examples of the support in the form of a sheet include a plastic film, a metal film, and a glass plate. Examples of materials of the plastic film include polyester such as polyethylene terephthalate (PET), polycarbonate, an acrylic resin, an epoxy resin, polyurethane, polyamide, polyolefin, cellulose derivatives, and silicone. Examples of the metal film include a copper film.

[Disk-Like Liquid Crystal Compound]

The disk-like liquid crystal compound according to an embodiment of the present invention has one or more reactive functional groups selected from the group consisting of a hydroxyl group, a carboxylic acid group, a carboxylic acid anhydride group, an amino group, a cyanate ester group, and a thiol group.

The definition of the disk-like compound and suitable aspects thereof as well as the reactive functional groups and suitable aspects thereof are as described above.

From the viewpoint of thermal conductivity, the molecular weight of the disk-like liquid crystal compound is preferably equal to or smaller than 3,000, and more preferably equal to or smaller than 2,500. The lower limit of the molecular weight is not particularly limited, but is equal to or greater than 200 for example.

In view of further improving thermal conductivity, the disk-like liquid crystal compound is preferably a compound represented by Formula (1A) which will be described later.

(1A)

In the formula, M represents an $n^{c1}$ valent disk-like core portion.

$L^{c11}$ represents a divalent linking group.

Q represents a hydrogen atom or a substituent.

$n^{c1}$ represents an integer equal to or greater than 3.

Here, one or more Q's represent the reactive functional group described above. In a case where M is a triphenylene skeleton, $L^{c11}$ represents a divalent linking group having a partial structure represented by $*^{c1}$-alkylene group-$X^{c1}$—$*^{c2}$, $*^{c1}$-$X^{c1}$-alkylene group-$*^{c2}$, or $*^{c1}$-$X^{c1}$-arylene group-O—$*^{c2}$.

$X^{c1}$ represents —O—C(=O)— or —C(=O)—O—.

$*^{c1}$ represents a position of binding to the disk-like core portion. $*^{c2}$ represents the other binding position.

M, $n^{c1}$, $L^{c11}$, and Q in Formula (1A) have the same definition as M, $n^{c1}$, $L^{c1}$, and Q in Formula (1) described above, and suitable aspects thereof are also the same.

As Formula (1A), particularly, a compound represented by Formula (D4A) or a compound represented by Formula (D16) is preferable.

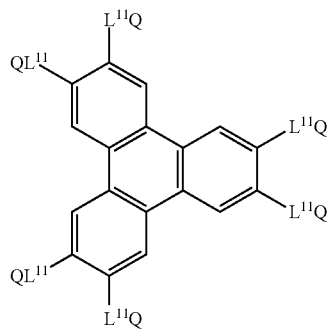

(D4A)

$L^{11}$ represents a divalent linking group having a partial structure represented by $*^{c1}$-alkylene group-$X^{c1}$—$*^{c2}$, $*^{c1}$-$X^{c1}$-alkylene group-$*^{c2}$, or $*^{c1}$-$X^{c1}$-arylene group-O—$*^{c2}$.

$X^{c1}$ represents —O—C(=O)— or —C(=O)—O—.

$*^{c1}$ represents a position of binding to the disk-like core portion. $*^{c2}$ represents the other binding position.

Q's each independently represent a hydrogen atom or a substituent.

One or more Q's represent the reactive functional group described above.

In Formula (D4A), $L^{11}$ corresponds to a divalent linking group represented by L in any of Formulae (D1) to (D15) that has a partial structure represented by $*^{c1}$-alkylene group-$X^{c1}$—$*^{c2}$, $*^{c1}$-$X^{c1}$-alkylene group-$*^{c2}$, or $*^{c1}$-$X^{c1}$-arylene group-O—$*^{c2}$. That is, examples of $L^{11}$ are the same as the examples of L in Formula (D4).

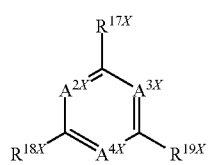

(D16)

In Formula (D16), $A^{2X}$, $A^{3X}$, and $A^{4X}$ each independently represent —CH= or —N=.

$R^{17X}$, $R^{18X}$, and $R^{19X}$ each independently represent $*$—$X^{211X}$—$(Z^{21X}$—$X^{212X})_{n21X}$-$L^{21X}$-Q. $*$ represents a position of binding to the central ring.

$X^{211X}$ and $X^{212X}$ each independently represent a single bond, —O—, —C(=O)—, —NH—, —OC(=O)—, —OC(=O)O—, —OC(=O)NH—, —OC(=O)S—, —C(=O)O—, —C(=O)NH—, —C(=O)S—, —NHC(=O)—, —NHC(=O)O—, —NHC(=O)NH—, —NHC(=O)S—, —S—, —SC(=O)—, —SC(=O)O—, —SC(=O)NH—, or —SC(=O)S—.

$Z^{21X}$'s each independently represent a 5-membered or 6-membered aromatic ring group or a 5-membered or 6-membered non-aromatic ring group.

$L^{21X}$ represents a single bond or a divalent linking group.

Q's each independently represent a hydrogen atom or a substituent.

Here, one or more Q's represent the reactive functional groups described above.

n21x represents an integer of 0 to 3. In a case where n21x is equal to or greater than 2, a plurality of groups represented by $(Z^{21X}$—$X^{212X})$ may be the same as or different from each other.

The compound represented by Formula (D16) is as described above.

From the viewpoint of curing reaction, the phase transition temperature of the disk-like liquid crystal compound, at which transition to a liquid crystal phase from a crystal phase occurs, is preferably equal to or lower than 200° C., and more preferably equal to or lower than 180° C. There is no particular limitation on the lower limit of the phase transition temperature at which transition to a liquid crystal phase from a crystal phase occurs. For example, the lower limit of the phase transition temperature is equal to or higher than 0° C. The phase transition temperature can be checked by observation using a polarizing microscope or by differential scanning calorimetry.

EXAMPLES

Hereinafter, the present invention will be more specifically described based on examples. The materials, the amounts of the materials used, the proportions of the materials, the details of treatments, and the procedures of treatments shown in the following examples can be appropriately changed as long as the gist of the present invention is maintained. Accordingly, the scope of the present invention is not limited to the following examples.

[Preparation and Evaluation (1) of Composition]

[Various Components]

Various components used in examples and comparative examples will be shown below.

<Disk-Like Compound or Rod-Like Compound>

(Synthesis of Disk-Like Compound B-1)

According to the following synthesis scheme, a disk-like compound B-1 was synthesized.

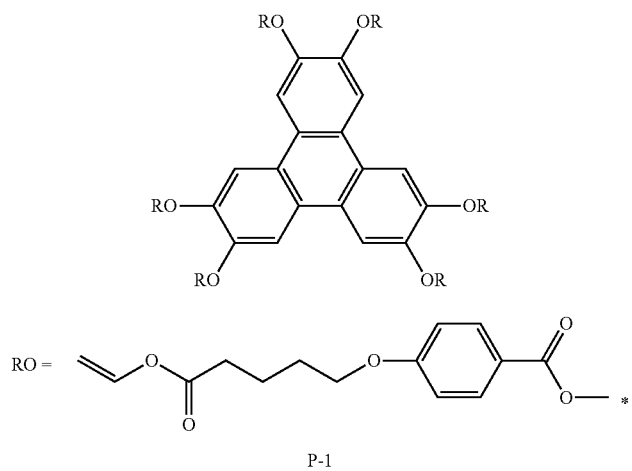
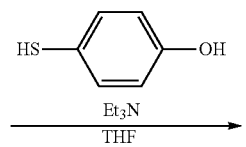

P-1

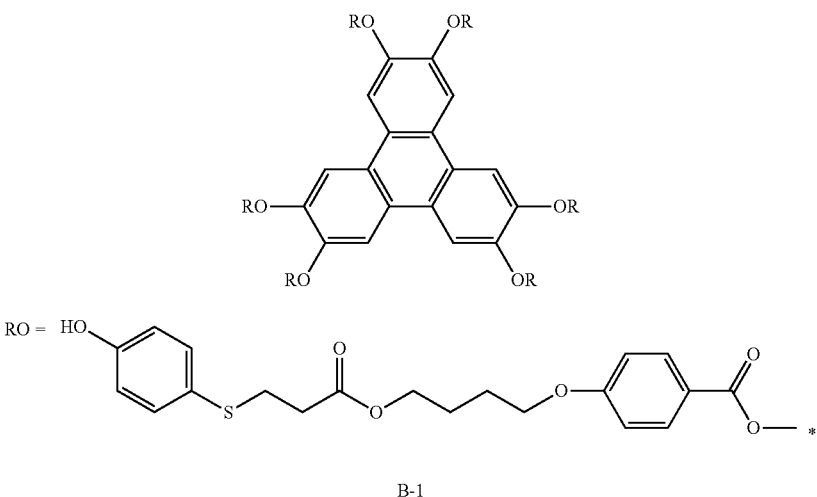

B-1

According to the method described on p. 1190 in the December issue (2002) of The Journal of The Society of Synthetic Organic Chemistry, a disk-like compound P-1 was synthesized. A mixed solution, which was obtained by mixing together P-1 (7 g), p-mercaptophenol (2.9 g), triethylamine (3.6 g), and tetrahydrofuran (70 mL) in a 300 mL three-neck flask, was stirred for 2 hours at room temperature. Distilled water (70 mL) was added to the mixed solution, and then a reaction product was extracted using ethyl acetate (70 mL). Furthermore, the extract was washed with 1 N hydrochloric acid (70 mL) and saturated saline (70 mL), and then moisture was removed from the extract by using anhydrous magnesium sulfate. The solvents in the extract were removed under reduced pressure, thereby obtaining the disk-like compound B-1 (9.5 g, yield: 95%).

Disk-like compounds B-2 to B-7, B-11 to B-18, and B-21 to B-23 were synthesized with reference to the synthesis method of the disk-like compound B-1.

(Synthesis of Disk-Like Compound B-8)

An example compound 13 was synthesized according to the method in Example 14 described in Japanese Patent No. 5620129 and adopted as a disk-like compound P-2 shown below. By using P-2, a disk-like compound B-8 was synthesized by the same method as the aforementioned method used for synthesizing the disk-like compound B-1.

Disk-like compounds P-9, P-10, and B-19 to P-20 were synthesized with reference to the synthesis method of the disk-like compound B-8.

P-2

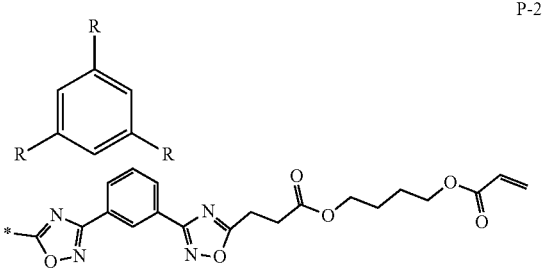

The structures of the obtained disk-like compounds B-1 to B-23 will be shown below.

In the structural formulae, * represents a position of binding to the central ring.

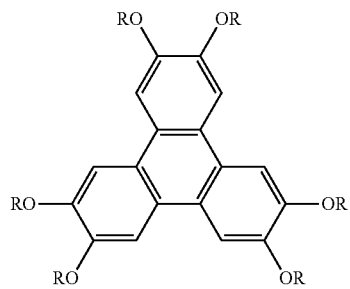
B-1 RO = 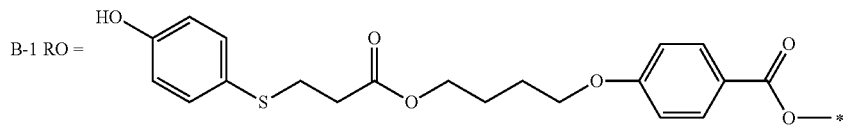
B-2 RO = 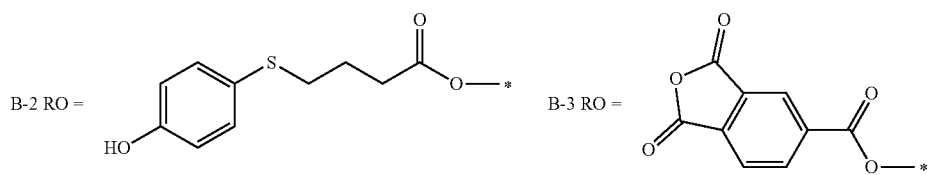  B-3 RO =
B-4 RO = 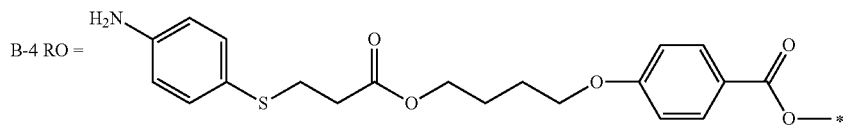
B-5 RO = 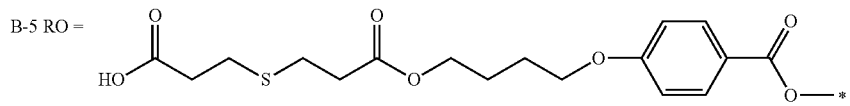
B-6 RO =   B-7 RO =
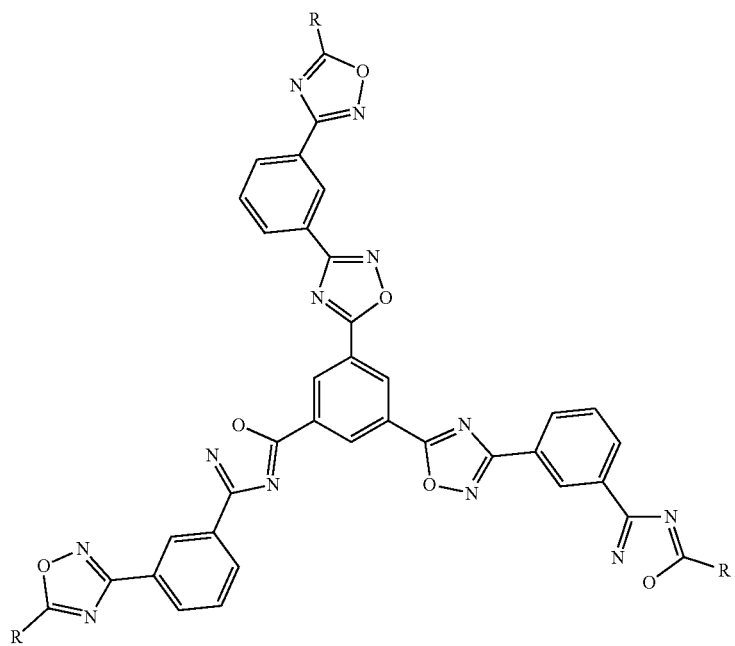

-continued
B-8 R = 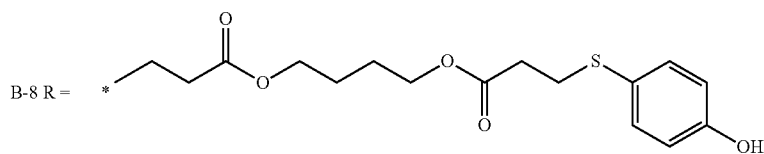
B-9 R = 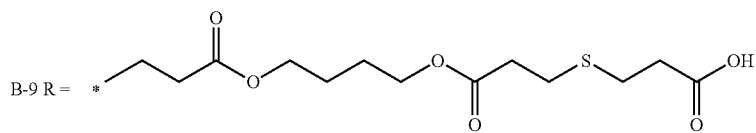
B-10 R = 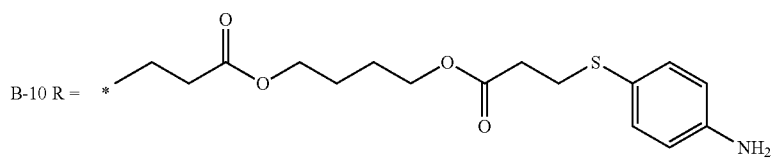
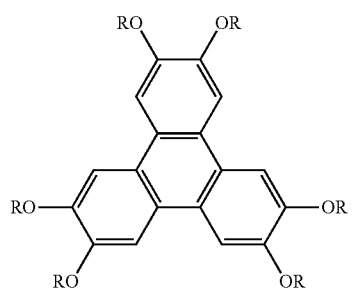
B-11 RO = 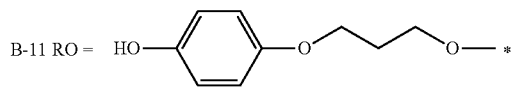
B-12 RO = 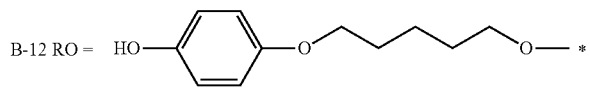
B-13 RO = 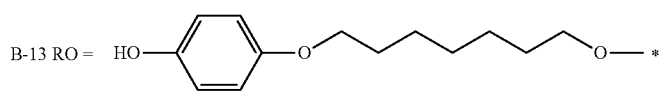
B-14 RO = 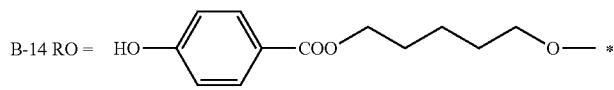
B-15 RO = 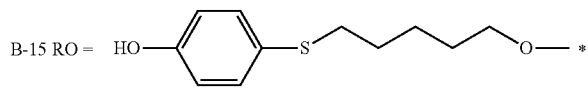
B-16 RO = 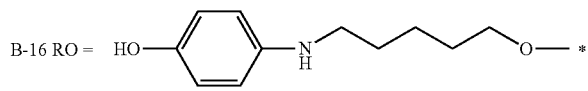
B-17 RO = 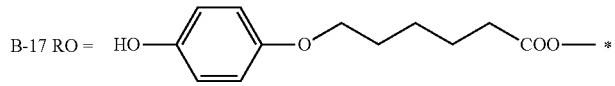
B-18 RO = 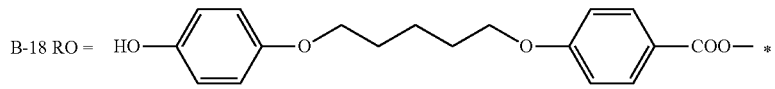

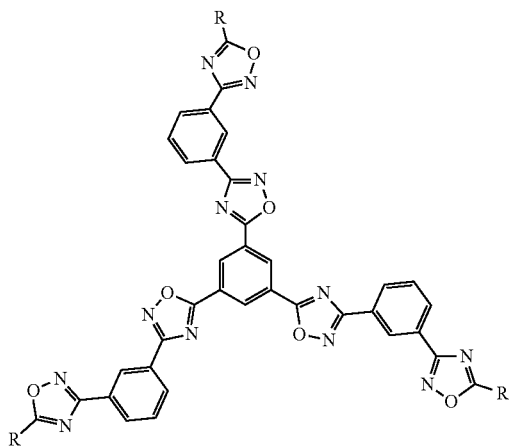
B-19 R = 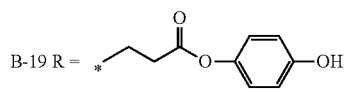
B-20 R = 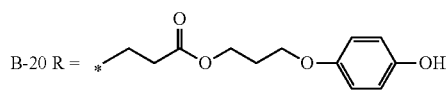
B-21
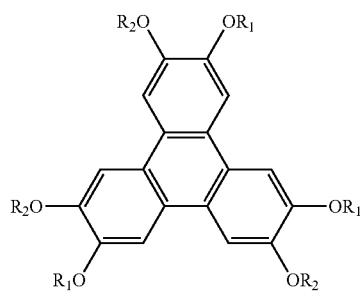
$R_1O =$ 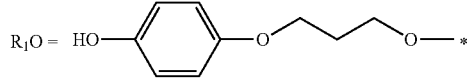
$R_2O =$ 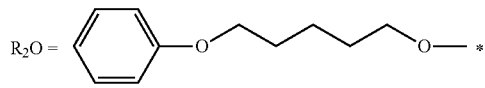
B-22
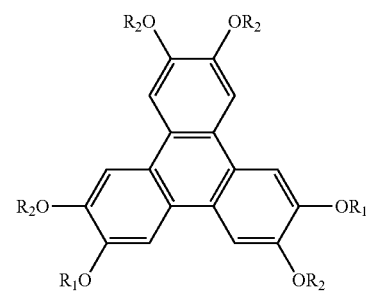
$R_1O =$ 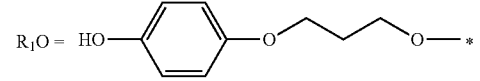
$R_2O =$ 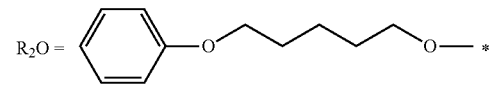
B-23
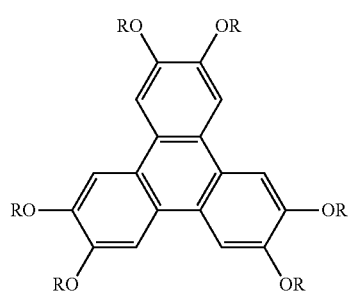
$RO =$ 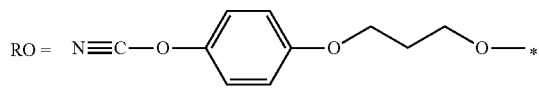

(Rod-Like Compound)

The structures of rod-like compounds D-1 and D-2 will be shown below.

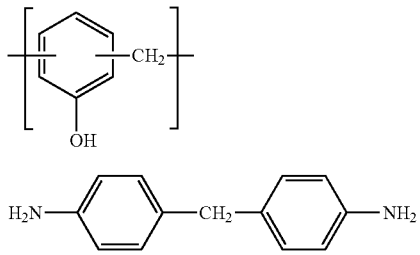

<Crosslinking Compound>

As crosslinking compounds, the following compounds A-1 to A-6 were used.

A-1: mixture of bisphenol F diglycidyl ether resin and bisphenol A diglycidyl ether resin, epoxy equivalents: 165.7 g/eq, total content of chlorine: 0.008% by weight, viscosity: 2,340 mPa·s, manufactured by NIPPON STEEL Chemical & Material Co., Ltd.

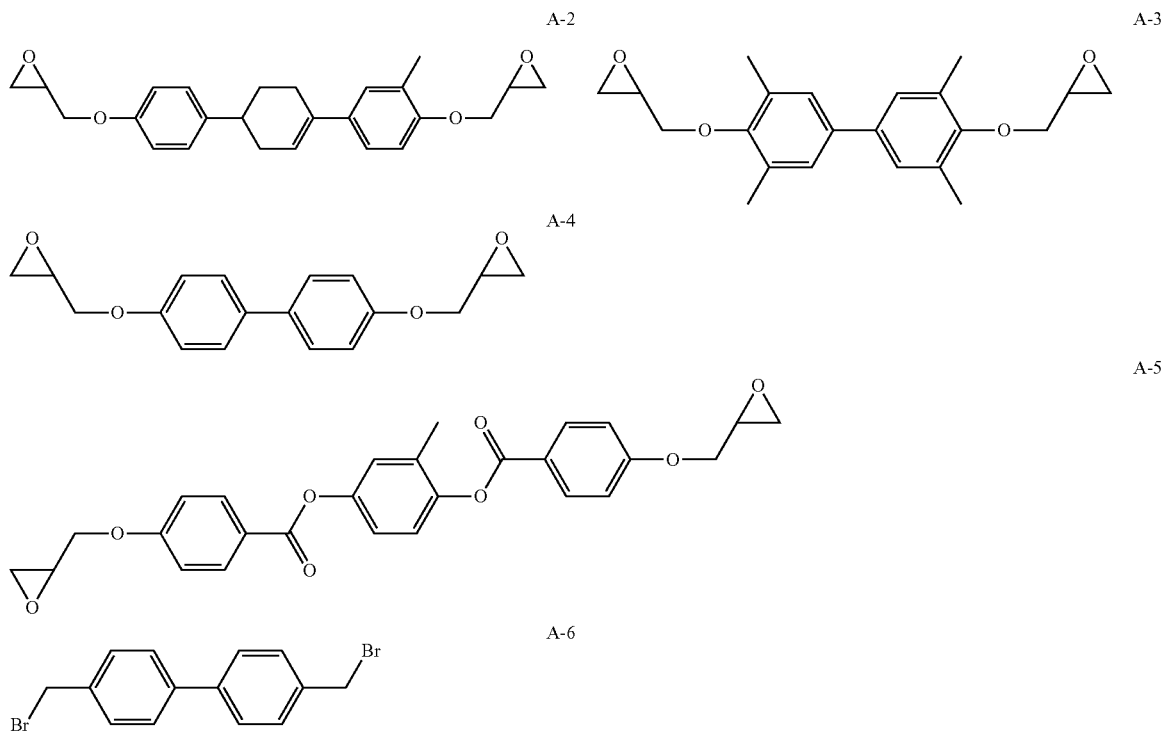

<Curing Accelerator>

As a curing accelerator, triphenylphosphine ($PPh_3$) was used.

<Inorganic Substance>

As an inorganic substance, SGPS (boron nitride, average particle diameter: 12 μm, manufactured by Denka Company Limited.) was used.

<Solvent>

As a solvent, methyl ethyl ketone (MEK) was used.

[Preparation]

Example 1

Various components shown in the following Table 1 were mixed together in order of the disk-like compound, methyl ethyl ketone (MEK), the crosslinking compound, and the curing accelerator, and then the inorganic substance was added thereto. The obtained mixture was treated for 5 minutes by using a rotation-revolution mixer (manufactured by THINKY CORPORATION, AWATORI RENTARO ARE-310), thereby obtaining a composition 1.

The mixing ratio between the disk-like compound and the crosslinking compound was adjusted such that the number of reactive functional groups contained in the disk-like compound in the composition became the same as the number of crosslinking groups contained in the crosslinking compound in the composition.

Furthermore, the final solid contents in the composition 1 were adjusted using MEK such that the solid contents had concentration (described in the column of "Solvent") described in Table 1.

Thereafter, by using an applicator, the composition 1 was uniformly applied to a release surface of a polyester film (NP-100A, manufactured by PANAC Corporation., film thickness: 100 μm), and left to stand in the air for 1 hour, thereby obtaining a coating film 1.

Subsequently, a surface to be coated of the coating film 1 was covered with another polyester film and treated by heat pressing in the air (treated for 30 minutes at a hot plate temperature of 160° C. and a pressure of 12 MPa and then treated for 2 hours at 190° C. and a pressure of 12 MPa) such that the coating film was cured, thereby obtaining a resin sheet. The polyester film was peeled from both surfaces of the resin sheet, thereby obtaining a thermally conductive sheet 1 having an average film thickness of 250 μm.

[Evaluation of Thermal Conductivity]

The thermal conductivity was evaluated using the thermally conductive sheet 1. The thermal conductivity was measured by the following method and evaluated according to the following standards.

(Measurement of Thermal Conductivity (W/m·k))

(1) By using "ai-Phase.Mobile 1u" manufactured by ai-Phase Co., Ltd., a coefficient of thermal diffusivity of the thermally conductive sheet 1 in a thickness direction was measured.

(2) By using a balance "XS204" manufactured by METTLER TOLEDO, the specific gravity of the thermally conductive sheet 1 was measured by the Archimedes method (using "solid specific gravity measuring kit").

(3) By using "DSC320/6200" manufactured by Seiko Instruments Inc., the specific heat of the thermally conductive sheet 1 at 25° C. was determined under the heating condition of 10° C./min.

(4) The obtained coefficient of thermal diffusivity was multiplied by the specific gravity and the specific heat, thereby calculating the thermal conductivity of the thermally conductive sheet 1.

(Evaluation Standards)

"A": equal to or higher than 15 W/m·k

"B": equal to or higher than 12 W/m·k and less than 15 W/m·k

"C": equal to or higher than 9 W/m·k and less than 12 W/m·k

"D": less than 9 W/m·k

The results are shown in Table 1.

Examples 2 to 29 and Comparative Examples 1 and 2

Compositions of examples and comparative examples shown in the following Table 1 were obtained according to the same procedure as in Example 1. In the comparative examples, instead of the disk-like compound, a rod-like compound D-1 or D-2 was used.

Furthermore, the final solid contents in the composition were adjusted using MEK such that the solid contents had concentration (described in the column of "Solvent") described in Table 1.

In addition, by using the obtained compositions, thermally conductive sheets 2 to 29 and comparative thermally conductive sheets 1 and 2 were prepared, and the test for evaluating thermal conductivity was performed in the same manner as in Example 1. The results are shown in Table 1.

In Table 1, (numbers) described in the columns for the components in various compositions mean the content (% by mass) of the components with respect to the total solid content in the composition.

Furthermore, "Film thickness [μm]" described in Table 1 means the average film thickness of the thermally conductive sheet.

"Central ring" described in Table 1 represents the structure of the central ring contained in the used disk-like compound.

"Reactive functional group" described in Table 1 represents the type of the reactive functional group that the used disk-like compound has.

"Number of functional groups" described in Table 1 represents the number of reactive functional groups that the used disk-like compound has.

"Crosslinking group" described in Table 1 represents the type of the crosslinking group that the used crosslinking compound has.

"Formula (E1)" described in Table 1 shows whether or not an epoxy compound is a compound represented by Formula (E1) in a case where an epoxy compound is used as a crosslinking compound. In a case where the used epoxy compound is the compound represented by Formula (E1), "Used" is described in the column of "Formula (E1)". In a case where the used epoxy compound is not the compound represented by Formula (E1), "Not used" is described in the column of "Formula (E1)".

TABLE 1

| | Composition | | | | | Disk-like compound | | |
|---|---|---|---|---|---|---|---|---|
| | Crosslinking compound (% by mass) | Disk-like compound or rod-like compound (% by mass) | Curing accelerator (% by mass) | Inorganic substance (% by mass) | Solvent (concentration of solid contents (% by mass)) | Central ring | Reactive functional group | Number of functional groups |
| Example 1 | A-3(11) | B-1(28) | PPh₃(1) | SGPS(60) | MEK(40) | Triphenylene ring | Hydroxyl group | 6 |
| Example 2 | A-3(16) | B-2(23) | PPh₃(1) | SGPS(60) | MEK(40) | Triphenylene ring | Hydroxyl group | 6 |
| Example 3 | A-3(17) | B-3(22) | PPh₃(1) | SGPS(60) | MEK(40) | Triphenylene ring | Carboxylic acid anhydride group | 6 |
| Example 4 | A-3(12) | B-4(28) | | SGPS(60) | MEK(40) | Triphenylene ring | Amino group | 6 |
| Example 5 | A-3(12) | B-5(27) | PPh₃(1) | SGPS(60) | MEK(40) | Triphenylene ring | Carboxylic acid group | 6 |
| Example 6 | A-3(17) | B-6(22) | PPh₃(1) | SGPS(60) | MEK(40) | Triphenylene ring | Hydroxyl group | 6 |
| Example 7 | A-3(17) | B-7(22) | PPh₃(1) | SGPS(60) | MEK(40) | Triphenylene ring | Hydroxyl group | 6 |
| Example 8 | A-3(9) | B-8(30) | PPh₃(1) | SGPS(60) | MEK(40) | Benzene ring | Hydroxyl group | 3 |
| Example 9 | A-3(10) | B-9(29) | PPh₃(1) | SGPS(60) | MEK(40) | Benzene ring | Carboxylic acid group | 3 |
| Example 10 | A-3(10) | B-10(30) | | SGPS(60) | MEK(40) | Benzene ring | Amino group | 3 |
| Example 11 | A-2(18) | B-6(21) | PPh₃(1) | SGPS(60) | MEK(40) | Triphenylene ring | Hydroxyl group | 6 |
| Example 12 | A-1(17) | B-6(22) | PPh₃(1) | SGPS(60) | MEK(40) | Triphenylene ring | Hydroxyl group | 6 |
| Example 13 | A-3(17) | B-6(22) | PPh₃(1) | SGPS(60) | MEK(40) | Triphenylene ring | Hydroxyl group | 6 |
| Example 14 | A-3(18) | B-11(21) | PPh₃(1) | SGPS(60) | MEK(40) | Triphenylene ring | Hydroxyl group | 6 |
| Example 15 | A-3(17) | B-12(22) | PPh₃(1) | SGPS(60) | MEK(40) | Triphenylene ring | Hydroxyl group | 6 |
| Example 16 | A-3(16) | B-13(23) | PPh₃(1) | SGPS(60) | MEK(40) | Triphenylene ring | Hydroxyl group | 6 |
| Example 17 | A-3(16) | B-14(23) | PPh₃(1) | SGPS(60) | MEK(40) | Triphenylene ring | Hydroxyl group | 6 |
| Example 18 | A-3(16) | B-15(23) | PPh₃(1) | SGPS(60) | MEK(40) | Triphenylene ring | Hydroxyl group | 6 |

TABLE 1-continued

| | | | | | | | | |
|---|---|---|---|---|---|---|---|---|
| Example 19 | A-3(17) | B-16(22) | PPh₃(1) | SGPS(60) | MEK(40) | Triphenylene ring | Hydroxyl group | 6 |
| Example 20 | A-3(16) | B-17(23) | PPh₃(1) | SGPS(60) | MEK(40) | Triphenylene ring | Hydroxyl group | 6 |
| Example 21 | A-3(13) | B-18(26) | PPh₃(1) | SGPS(60) | MEK(40) | Triphenylene ring | Hydroxyl group | 6 |
| Example 22 | A-3(12) | B-19(27) | PPh₃(1) | SGPS(60) | MEK(40) | Benzene ring | Hydroxyl group | 3 |
| Example 23 | A-3(11) | B-20(28) | PPh₃(1) | SGPS(60) | MEK(40) | Benzene ring | Hydroxyl group | 3 |
| Example 24 | A-4(16) | B-11(23) | PPh₃(1) | SGPS(60) | MEK(40) | Triphenylene ring | Hydroxyl group | 6 |
| Example 25 | A-5(21) | B-11(18) | PPh₃(1) | SGPS(60) | MEK(40) | Triphenylene ring | Hydroxyl group | 6 |
| Example 26 | A-3(12) | B-21(27) | PPh₃(1) | SGPS(60) | MEK(40) | Triphenylene ring | Hydroxyl group | 3 |
| Example 27 | A-3(8) | B-22(31) | PPh₃(1) | SGPS(60) | MEK(40) | Triphenylene ring | Hydroxyl group | 2 |
| Example 28 | A-6(18) | B-11(21) | PPh₃(1) | SGPS(60) | MEK(40) | Triphenylene ring | Hydroxyl group | 6 |
| Example 29 | A-3(17) | B-23(22) | PPh₃(1) | SGPS(60) | MEK(40) | Triphenylene ring | Cyanate ester group | 6 |
| Comparative Example 1 | A-1(18) | D-1(21) | PPh₃(1) | SGPS(60) | MEK(40) | — | — | — |
| Comparative Example 2 | A-1(24) | D-2(15) | PPh₃(1) | SGPS(60) | MEK(40) | — | — | — |

| | Crosslinking compound | | Evaluation | |
|---|---|---|---|---|
| | Crosslinking group | Formula (E1) | Thermal conductivity | Film thickness [μm] |
| Example 1 | Oxiranyl group | Used | A | 250 |
| Example 2 | Oxiranyl group | Used | A | 250 |
| Example 3 | Oxiranyl group | Used | A | 250 |
| Example 4 | Oxiranyl group | Used | B | 250 |
| Example 5 | Oxiranyl group | Used | A | 250 |
| Example 6 | Oxiranyl group | Used | A | 250 |
| Example 7 | Oxiranyl group | Used | A | 250 |
| Example 8 | Oxiranyl group | Used | B | 250 |
| Example 9 | Oxiranyl group | Used | B | 250 |
| Example 10 | Oxiranyl group | Used | C | 250 |
| Example 11 | Oxiranyl group | Used | A | 250 |
| Example 12 | Oxiranyl group | Not used | B | 250 |
| Example 13 | Oxiranyl group | Used | A | 250 |
| Example 14 | Oxiranyl group | Used | A | 250 |
| Example 15 | Oxiranyl group | Used | A | 250 |
| Example 16 | Oxiranyl group | Used | A | 250 |
| Example 17 | Oxiranyl group | Used | A | 250 |
| Example 18 | Oxiranyl group | Used | A | 250 |
| Example 19 | Oxiranyl group | Used | A | 250 |
| Example 20 | Oxiranyl group | Used | A | 250 |
| Example 21 | Oxiranyl group | Used | A | 250 |
| Example 22 | Oxiranyl group | Used | B | 250 |
| Example 23 | Oxiranyl group | Used | B | 250 |
| Example 24 | Oxiranyl group | Used | A | 250 |
| Example 25 | Oxiranyl group | Used | A | 250 |
| Example 26 | Oxiranyl group | Used | B | 250 |
| Example 27 | Oxiranyl group | Used | C | 250 |
| Example 28 | Halogenated benzyl group | — | C | 250 |
| Example 29 | Oxiranyl group | Used | B | 250 |
| Comparative Example 1 | Oxiranyl group | Not used | D | 250 |
| Comparative Example 2 | Oxiranyl group | Not used | D | 250 |

As shown in the above table, it has been confirmed that the thermally conductive material according to the embodiment of the present invention has excellent thermal conductivity.

Furthermore, it has been confirmed that in a case where the specific disk-like compound has a triphenylene ring as the central ring, the thermal conductivity of the thermally conductive material is further improved (comparison of Examples 8 to 10, 22, and 23 with other examples).

It has been confirmed that in a case where the specific disk-like compound has 3 to 6 reactive functional groups, the thermal conductivity of the thermally conductive material is further improved (comparison of Example 27 with other examples).

It has been confirmed that in a case where the reactive functional group that the specific disk-like compound has is any of the hydroxyl group, the carboxylic acid group, and the carboxylic acid anhydride group, the thermal conductivity of the thermally conductive material is further improved (comparison of Examples 4 and 10 with other examples).

It has been confirmed that in a case where the crosslinking compound is an epoxy compound, the thermal conductivity of the thermally conductive material is further improved (comparison of Example 28 with other examples).

It has been confirmed that in a case where the epoxy compound is represented by Formula (E1), the thermal conductivity of the thermally conductive material is further improved (comparison of Example 12 with other examples).

[Preparation and Evaluation (2) of Composition]

According to the following procedure, a composition, which contained a disk-like compound having one or more reactive functional groups selected from the group consisting of a hydroxyl group, a carboxylic acid group, a carboxylic acid anhydride group, an amino group, a cyanate ester group, and a thiol group and a crosslinking compound, was prepared and evaluated. Hereinafter, the crosslinking compound will be described as "main agent", and the disk-like compound will be described as "curing agent"

[Various Components]

Various components used in examples, which will be described later, will be shown below.

<Curing Agent>

Disk-like compounds C-1 to C-15 will be shown below. In the structural formulae, * represents a position of binding to the central ring. Among the disk-like compounds C-1 to C-15, C-1 to C-12 and C-15 exhibit liquid crystallinity (that is, C-1 to C-12 and C-15 correspond to disk-like liquid crystal compounds). As an example of a method for synthesizing a disk-like liquid crystal compound, a synthesis example of C-5 will be shown later.

Disk-like compounds C-1 to C-15 will be shown below. In the structural formulae, * represents a position of binding to the central ring.

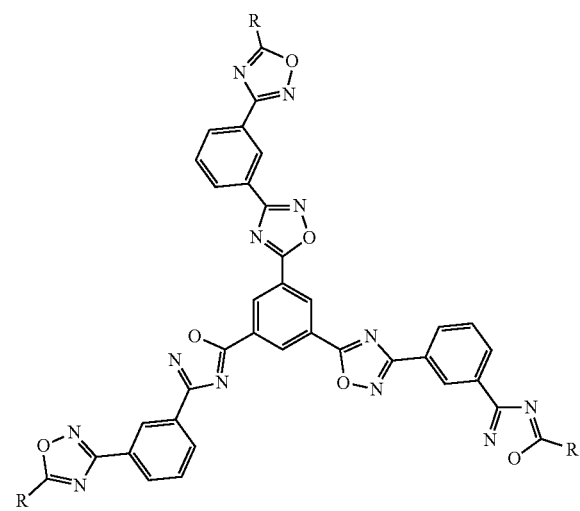

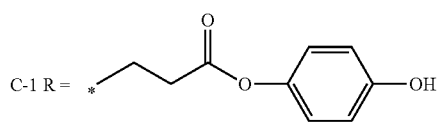

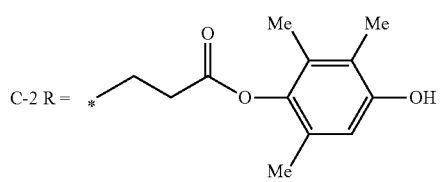

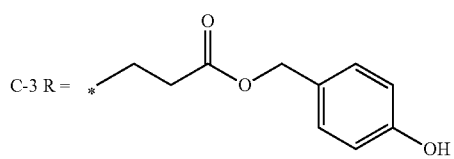

-continued

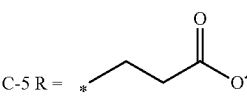

C-14

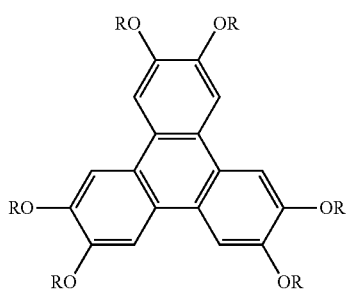

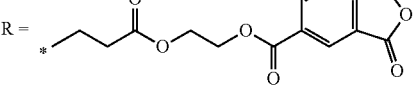

(Synthesis Example)

<<Synthesis of Disk-Like Liquid Crystal Compound C-5>>

According to the method described in Japanese Patent No. 5385937, a disk-like carboxylic acid was synthesized. The disk-like carboxylic acid (20 g) and DMAc (100 mL) were put into a 500 mL three-neck flask, and then thionyl chloride (9.2 g) was added dropwise thereto at a temperature of 5° C. to 15° C. The resulting solution was stirred for 2 hours at room temperature, and then a mixed solution of p-hydroxyphenethyl alcohol (12.5 mL) and DMAc (10 mL) was added dropwise thereto at a temperature of 5° C. to 15° C., and the solution was stirred for 2 hours at room temperature. Distilled water (100 mL), ethyl acetate (200 mL), and hexane (50 mL) were added to the mixed solution, and the reaction product was extracted. The extract was washed with saturated saline (100 mL), and then moisture was removed from the extract by using anhydrous magnesium sulfate. Solvents were removed from the extract under reduced pressure, and the remaining solids were purified by column chromatography (hexane/ethyl acetate=3/7), thereby obtaining a disk-like compound C-5 (17.7 g, yield: 64%).

C-15

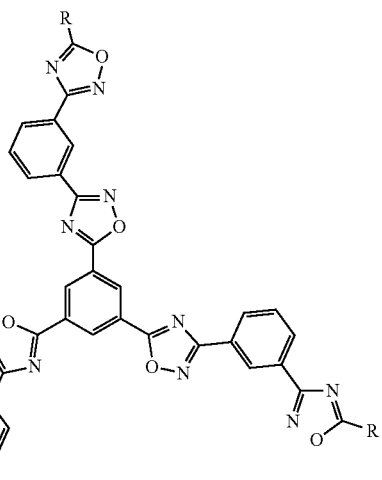

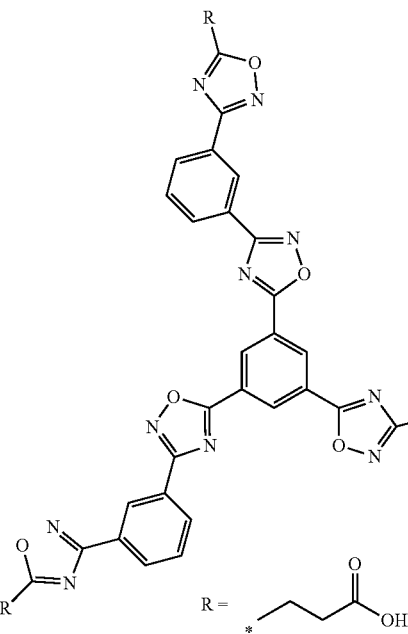

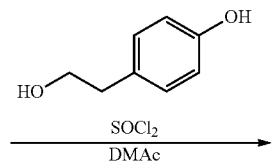

-continued

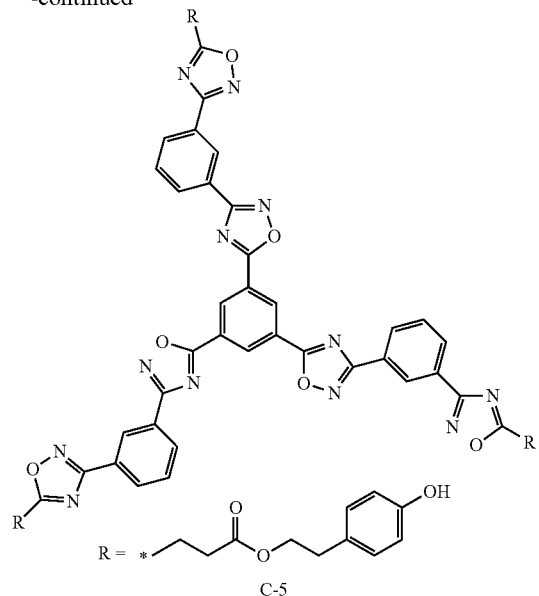

C-5

(Liquid Crystallinity of Curing Agent)

Each of the curing agents (C-1 to C-15) was independently heated on a hot stage. By using a polarizing microscope, the behavior of phase transition (crystal-liquid crystal phase transition temperature) was observed.

Table 2 shows whether or not the curing agents exhibit liquid crystallinity, the type of liquid crystal phase, and the crystal-liquid crystal phase transition temperature. In Table 2, "N/A" means that the curing agent does not exhibit liquid crystallinity. Furthermore, in Table 2, "$D_{Ne}$" means discotic nematic phase.

<Main Agent (Crosslinking Compound)>

As main agents, the following compounds D-1 to D-8 were used.

D-1: mixture of bisphenol F diglycidyl ether resin and bisphenol A diglycidyl ether resin, epoxy equivalents: 165.7 g/eq, total content of chlorine: 0.008% by mass, viscosity: 2,340 mPa·s, manufactured by NIPPON STEEL Chemical & Material Co., Ltd.

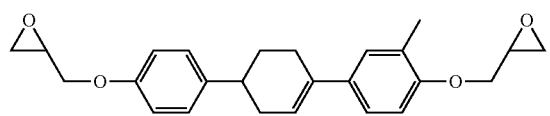

D-2

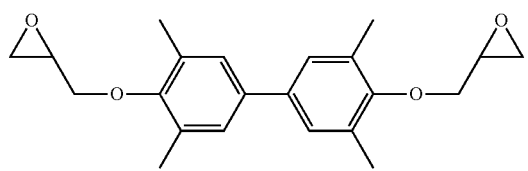

D-3

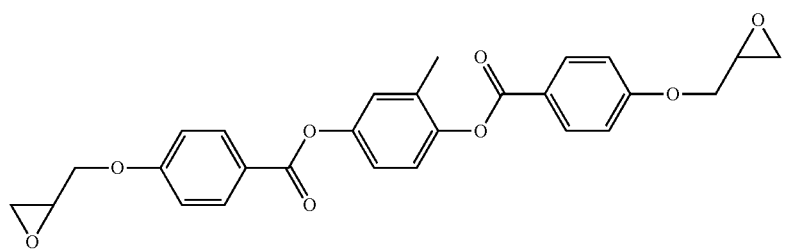

D-4

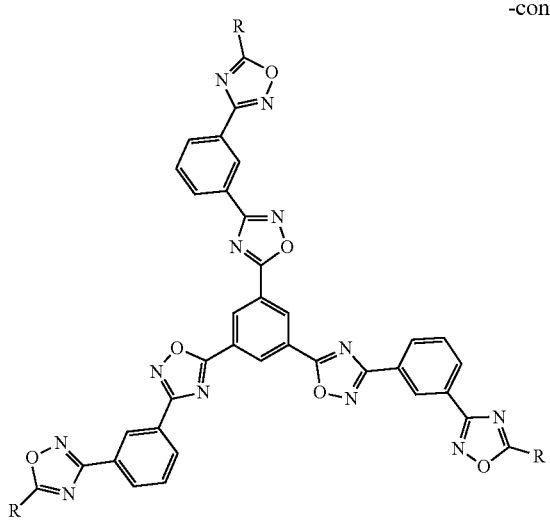

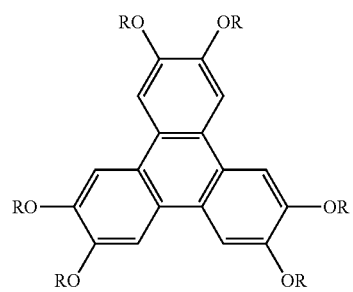

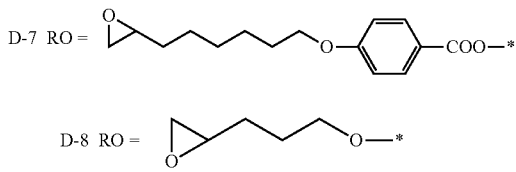

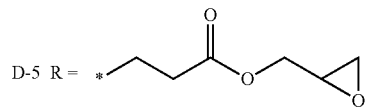

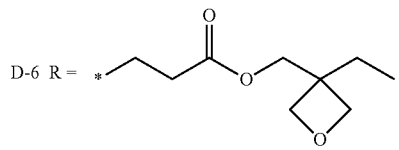

(Liquid Crystallinity of Main Agent)

Each of the main agents (D-1 to D-8) was independently heated on a hot stage. By using a polarizing microscope, the behavior of phase transition was observed.

Table 2 shows whether or not the main agents exhibit liquid crystallinity and the type of liquid crystal phase. In Table 2, "N/A" means that the main agent does not exhibit liquid crystallinity, "$D_{Ne}$" means discotic nematic phase, and "Ne" means nematic phase.

<Curing Accelerator>

As a curing accelerator, triphenylphosphine ($PPh_3$) was used.

<Inorganic Substance>

"PTX-60": aggregated boron nitride (average particle diameter: 60 μm, manufactured by Momentive)

"PT-110": flat plate-like boron nitride (average particle diameter: 45 μm, manufactured by Momentive)

"S-50": aluminum nitride (average particle diameter: 55 m, manufactured by MARUWA CO., LTD.)

"SGPS": boron nitride (average particle diameter: 12 μm, manufactured by Denka Company Limited.)

"AA-3": alumina (average particle diameter: 3 μm, manufactured by Sumitomo Chemical Co., Ltd.)

"AA-04": alumina (average particle diameter: 0.4 μm, manufactured by Sumitomo Chemical Co., Ltd.)

<Solvent>

As a solvent, tetrahydrofuran (THF) was used.

[Preparation]

Example 30

Various components shown in the following Table 2 were mixed together in order of the curing agent (disk-like liquid crystal compound), tetrahydrofuran (THF), the main agent (crosslinking compound), and the curing accelerator, and then the inorganic substance was added thereto. The obtained mixture was treated for 5 minutes by using a rotation-revolution mixer (manufactured by THINKY CORPORATION, AWATORI RENTARO ARE-310), thereby obtaining a composition 30.

Furthermore, the final solid contents in the composition 30 were adjusted using THF such that the solid contents had concentration (described in the column of "Solvent") described in Table 2.

Thereafter, by using an applicator, the composition 30 was uniformly applied to a release surface of a polyester film (NP-100A, manufactured by PANAC Corporation., film thickness: 100 μm), and left to stand in the air for 1 hour, thereby obtaining a coating film 30.

Subsequently, a surface to be coated of the coating film 30 was covered with another polyester film and treated by heat pressing in the air (treated for 30 minutes at a hot plate temperature of 170° C. and a pressure of 12 MPa and then treated for 2 hours at 190° C.) such that the coating film was cured, thereby obtaining a resin sheet. The polyester film was peeled from both surfaces of the resin sheet, thereby obtaining a thermally conductive sheet 30 having an average film thickness of 400 μm.

<Liquid Crystallinity of Composition 30>

The coating film 30 was heated on a hot stage. After heating, the composition was cooled, and in this state, the liquid crystallinity thereof was observed with a polarizing microscope.

Table 2 shows whether or not the composition exhibits liquid crystallinity and the type of liquid crystal phase.

[Evaluation of Thermal Conductivity]

By using the thermally conductive sheet 30, thermal conductivity was evaluated. The thermal conductivity was measured by the same method as that in Example 1 and evaluated according to the following evaluation standards.

(Evaluation Standards)
"A": equal to or higher than 15 W/m·k
"B++": equal to or higher than 13 W/m·k and less than 15 W/m·k
"B+": equal to or higher than 11 W/m·k and less than 13 W/m·k
"B": equal to or higher than 9 W/m·k and less than 11 W/m·k
"C": equal to or higher than 7 W/m·k and less than 9 W/m·k
"D": less than 7 W/m·k

[Evaluation of Heat Resistance]

By using the thermally conductive sheet 30, heat resistance was evaluated.

Specifically, the thermally conductive sheet 30 was heated for 1,000 hours at 175° C., and then the thermal conductivity was measured. Thereafter, a difference between the thermal conductivity before heating and the conductivity after heating was calculated and evaluated according to the following evaluation standards. The smaller the difference in the thermal conductivity, the higher the grade of evaluation.

(Evaluation Standards)
"A": less than 0.5 W/m·k
"B": equal to or higher than 0.5 W/m·k and less than 1.0 W/m·k
"C": equal to or higher than 1.0 W/m·k and less than 1.5 W/m·k
"D": equal to or higher than 1.5 W/m·k Examples 31 to 53

According to the same procedure as that in Example 31, compositions of examples and comparative examples shown in the following Table 2 were obtained. Furthermore, the final solid contents in the composition were adjusted using THF such that the solid contents had concentration (described in the column of "Solvent") described in Table 2.

By using the obtained compositions, thermally conductive sheets 31 to 53 were prepared, and the test for evaluating thermal conductivity was performed in the same manner as in Example 30. The results are shown in Table 2.

In addition, for Examples 31 to 53, whether or not the compositions exhibit liquid crystallinity and the type of liquid crystal phase were investigated by the same method as that in Example 30.

In Table 2, (numbers) described in the columns for the components in various compositions mean the content (% by mass) of various components with respect to the total solid content in the composition.

"Reactive functional group" described in Table 2 represents the type of the reactive functional group that the used curing agent (disk-like liquid crystal compound) has.

"Central ring" described in Table 2 shows the structure of the central ring that the used disk-like compound has.

"Liquid crystallinity" described in Table 2 shows whether or not each of the compounds as the main agent and the curing agent exhibits liquid crystallinity in a state where the compound is present as an independent compound. In Table 2, "N/A" means that the compound does not exhibit liquid crystallinity, "$D_{Ne}$" means discotic nematic phase, and "Ne" means nematic phase.

"Formula (1A)" described in Table 2 shows whether or not the used curing agent is the disk-like liquid crystal compound represented by Formula (1A). In a case where the used curing agent is the disk-like liquid crystal compound represented by Formula (1A), "Used" is described in the column of "Formula (1A)". In a case where the used curing agent is not the disk-like liquid crystal compound represented by Formula (1A), "Not used" is described in the column of "Formula (1A)".

"Crosslinking group" described in Table 2 shows the type of crosslinking group that the used main agent (crosslinking compound) has.

Furthermore, "Film thickness [μm]" described in Table 2 means the average film thickness of the thermally conductive sheet.

TABLE 2

| | Composition | | | | | | | | | |
|---|---|---|---|---|---|---|---|---|---|---|
| | Curing agent | | | | | | Main agent (crosslinking compound) | | | |
| | | | | | Phase transition | | | | | |
| | Type (% by mass) | Reactive functional group | Central ring | Liquid crystallinity | temperature of crystal phase-liquid crystal phase (° C.) | Formula (1A) | Type (% by mass) | Structure | Crosslinking group | Liquid crystallinity |
| Example 30 | C-1(29) | Hydroxyl group | Benzene ring | $D_{Ne}$ | Equal to or lower than 180° C. | Used | D-1(10) | Rod like (not corresponding to Formula (E1)) | Oxiranyl group | N/A |
| Example 31 | C-1(29) | Hydroxyl group | Benzene ring | $D_{Ne}$ | Equal to or lower than 180° C. | Used | D-2(10) | Rod like (corresponding to Formula (E1)) | Oxiranyl group | Ne |
| Example 32 | C-1(29) | Hydroxyl group | Benzene ring | $D_{Ne}$ | Equal to or lower than 180° C. | Used | D-3(10) | Rod like (corresponding to Formula (E1)) | Oxiranyl group | N/A |
| Example 33 | C-1(29) | Hydroxyl group | Benzene ring | $D_{Ne}$ | Equal to or lower than 180° C. | Used | D-4(10) | Rod like (corresponding to Formula (E1)) | Oxiranyl group | Ne |
| Example 34 | C-1(22) | Hydroxyl group | Benzene ring | $D_{Ne}$ | Equal to or lower than 180° C. | Used | D-5(17) | Disk-like compound | Oxiranyl group | $D_{Ne}$ |
| Example 35 | C-2(22) | Hydroxyl group | Benzene ring | $D_{Ne}$ | Equal to or lower than 180° C. | Used | D-5(17) | Disk-like compound | Oxiranyl group | $D_{Ne}$ |
| Example 36 | C-1(22) | Hydroxyl group | Benzene ring | $D_{Ne}$ | Equal to or lower than 180° C. | Used | D-8(17) | Disk-like compound | Oxiranyl group | $D_{Ne}$ |

TABLE 2-continued

| | | | | | | | | | | |
|---|---|---|---|---|---|---|---|---|---|---|
| Example 37 | C-3(22) | Hydroxyl group | Benzene ring | $D_{Ne}$ | Equal to or lower than 180° C. | Used | D-5(17) | Disk-like compound | Oxiranyl group | $D_{Ne}$ |
| Example 38 | C-4(22) | Hydroxyl group | Benzene ring | $D_{Ne}$ | 190° C. | Used | D-5(17) | Disk-like compound | Oxiranyl group | $D_{Ne}$ |
| Example 39 | C-5(22) | Hydroxyl group | Benzene ring | $D_{Ne}$ | Equal to or lower than 180° C. | Used | D-5(17) | Disk-like compound | Oxiranyl group | $D_{Ne}$ |
| Example 40 | C-6(22) | Carboxylic acid group | Benzene ring | $D_{Ne}$ | Equal to or lower than 180° C. | Used | D-5(17) | Disk-like compound | Oxiranyl group | $D_{Ne}$ |
| Example 41 | C-7(22) | Thiol group | Benzene ring | $D_{Ne}$ | Equal to or lower than 180° C. | Used | D-5(17) | Disk-like compound | Oxiranyl group | $D_{Ne}$ |
| Example 42 | C-8(22) | Hydroxyl group | Benzene ring | $D_{Ne}$ | Equal to or lower than 180° C. | Used | D-5(17) | Disk-like compound | Oxiranyl group | $D_{Ne}$ |
| Example 43 | C-9(22) | Amino group | Benzene ring | $D_{Ne}$ | Equal to or lower than 180° C. | Used | D-5(17) | Disk-like compound | Oxiranyl group | $D_{Ne}$ |
| Example 44 | C-10(22) | Cyanate ester group | Benzene ring | $D_{Ne}$ | Equal to or lower than 180° C. | Used | D-5(17) | Disk-like compound | Oxiranyl group | $D_{Ne}$ |
| Example 45 | C-11(22) | Hydroxyl group | Triphenylene ring | $D_{Ne}$ | Equal to or lower than 180° C. | Used | D-7(17) | Disk-like compound | Oxiranyl group | $D_{Ne}$ |
| Example 46 | C-12(22) | Hydroxyl group | Triphenylene ring | $D_{Ne}$ | Equal to or lower than 180° C. | Used | D-7(17) | Disk-like compound | Oxiranyl group | $D_{Ne}$ |
| Example 47 | C-1(22) | Hydroxyl group | Benzene ring | $D_{Ne}$ | Equal to or lower than 180° C. | Used | D-6(17) | Disk-like compound | Oxiranyl group | $D_{Ne}$ |
| Example 48 | C-13(22) | Hydroxyl group | Triphenylene ring | N/A | — | Not used | D-8(17) | Disk-like compound | Oxiranyl group | $D_{Ne}$ |
| Example 49 | C-14(22) | Hydroxyl group | Triphenylene ring | N/A | — | Not used | D-7(17) | Disk-like compound | Oxiranyl group | $D_{Ne}$ |
| Example 50 | C-15(22) | Carboxylic acid anhydride group | Benzene ring | $D_{Ne}$ | Equal to or lower than 180° C. | Used | D-5(17) | Disk-like compound | Oxiranyl group | $D_{Ne}$ |
| Example 51 | C-2(22) | Hydroxyl group | Benzene ring | $D_{Ne}$ | Equal to or lower than 180° C. | Used | D-5(17) | Disk-like compound | Oxiranyl group | $D_{Ne}$ |
| Example 52 | C-2(22) | Hydroxyl group | Benzene ring | $D_{Ne}$ | Equal to or lower than 180° C. | Used | D-5(17) | Disk-like compound | Oxiranyl group | $D_{Ne}$ |
| Example 53 | C-2(22) | Hydroxyl group | Benzene ring | $D_{Ne}$ | Equal to or lower than 180° C. | Used | D-5(17) | Disk-like compound | Oxiranyl group | $D_{Ne}$ |

| | Composition | | Solvent (concentration of solid contents (% by mass)) | Liquid crystallinity of composition | Evaluation | | |
|---|---|---|---|---|---|---|---|
| | Curing accelerator (% by mass) | Inorganic substance (% by mass) | | | Thermal conductivity | Film thickness [μm] | Heat resistance |
| Example 30 | PPh$_3$(1) | SGPS/AA3/AA04 = 30/20/10(60) | THF(40) | N/A | C | 400 | B |
| Example 31 | PPh$_3$(1) | SGPS/AA3/AA04 = 30/20/10(60) | THF(40) | N/A | A | 400 | B |
| Example 32 | PPh$_3$(1) | SGPS/AA3/AA04 = 30/20/10(60) | THF(40) | N/A | B | 400 | B |
| Example 33 | PPh$_3$(1) | SGPS/AA3/AA04 = 30/20/10(60) | THF(40) | N/A | A | 400 | B |
| Example 34 | PPh$_3$(1) | SGPS/AA3/AA04 = 30/20/10(60) | THF(40) | $D_{Ne}$ | A | 400 | A |
| Example 35 | PPh$_3$(1) | SGPS/AA3/AA04 = 30/20/10(60) | THF(40) | $D_{Ne}$ | A | 400 | A |
| Example 36 | PPh$_3$(1) | SGPS/AA3/AA04 = 30/20/10(60) | THF(40) | N/A | B | 400 | B |
| Example 37 | PPh$_3$(1) | SGPS/AA3/AA04 = 30/20/10(60) | THF(40) | $D_{Ne}$ | A | 400 | A |
| Example 38 | PPh$_3$(1) | SGPS/AA3/AA04 = 30/20/10(60) | THF(40) | $D_{Ne}$ | B | 400 | A |
| Example 39 | PPh$_3$(1) | SGPS/AA3/AA04 = 30/20/10(60) | THF(40) | $D_{Ne}$ | A | 400 | A |
| Example 40 | PPh$_3$(1) | SGPS/AA3/AA04 = 30/20/10(60) | THF(40) | $D_{Ne}$ | A | 400 | A |
| Example 41 | PPh$_3$(1) | SGPS/AA3/AA04 = 30/20/10(60) | THF(40) | $D_{Ne}$ | B++ | 400 | A |
| Example 42 | PPh$_3$(1) | SGPS/AA3/AA04 = 30/20/10(60) | THF(40) | $D_{Ne}$ | A | 400 | A |
| Example 43 | PPh$_3$(1) | SGPS/AA3/AA04 = 30/20/10(60) | THF(40) | $D_{Ne}$ | B+ | 400 | A |
| Example 44 | PPh$_3$(1) | SGPS/AA3/AA04 = 30/20/10(60) | THF(40) | $D_{Ne}$ | B++ | 400 | A |
| Example 45 | PPh$_3$(1) | SGPS/AA3/AA04 = 30/20/10(60) | THF(40) | $D_{Ne}$ | A | 400 | A |

TABLE 2-continued

| | | | | | | | | |
|---|---|---|---|---|---|---|---|---|
| Example 46 | PPh₃(1) | SGPS/AA3/AA04 = 30/20/10(60) | THF(40) | $D_{Ne}$ | A | 400 | A | |
| Example 47 | PPh₃(1) | SGPS/AA3/AA04 = 30/20/10(60) | THF(40) | $D_{Ne}$ | B++ | 400 | A | |
| Example 48 | PPh₃(1) | SGPS/AA3/AA04 = 30/20/10(60) | THF(40) | N/A | D | 400 | C | |
| Example 49 | PPh₃(1) | SGPS/AA3/AA04 = 30/20/10(60) | THF(40) | N/A | D | 400 | B | |
| Example 50 | PPh₃(1) | SGPS/AA3/AA04 = 30/20/10(60) | THF(40) | $D_{Ne}$ | A | 400 | A | |
| Example 51 | PPh₃(1) | PTX-60/AA3/AA04 = 30/20/10(60) | THF(40) | $D_{Ne}$ | A | 400 | A | |
| Example 52 | PPh₃(1) | PT110/AA3/AA04 = 30/20/10(60) | THF(40) | $D_{Ne}$ | A | 400 | A | |
| Example 53 | PPh₃(1) | S-50/AA3/AA04 = 30/20/10(60) | THF(40) | $D_{Ne}$ | B | 400 | A | |

As shown in the above table, it has been confirmed that even though the thermally conductive material using the disk-like liquid crystal compound (curing agent) according to the embodiment of the present invention has a film thickness of 400 μm, the thermal conductivity is further improved (comparison of Examples 30 to 47 and 49 to 53 with Examples 48 and 49).

By comparing Examples 34, 35, and 37 to 39 with Example 42, it has been confirmed that in a case where the crystal-liquid crystal phase transition temperature of the disk-like liquid crystal compound is equal to or lower than 180° C., the thermal conductivity is markedly improved.

Furthermore, it has been confirmed that in a case where the reactive functional group that the disk-like liquid crystal compound (curing agent) has is any of the hydroxyl group, the carboxylic acid group, and the carboxylic acid anhydride group, the thermal conductivity of the thermally conductive material is further improved (comparison of Examples 34, 35, 37, 39 to 44 and 50 with each other).

It has been confirmed that in a case where the crosslinking compound (main agent) has an epoxy group as a crosslinking group and is represented by Formula (E1) or in a case where the crosslinking compound is a disk-like compound having an epoxy group as a crosslinking group, the thermal conductivity of the thermally conductive material is further improved (comparison of Examples 30 and 32 with Example 36 and comparison of Example 46 with Example 47). Furthermore, it has been confirmed that in a case where both the curing agent and main agent exhibit liquid crystallinity, the thermal conductivity of the thermally conductive material is further improved (comparison of Example 31 with Example 32 and of Example 35 with Example 36).

As is evident from the results of Example 30 to Example 53, in a case where the composition for forming a thermally conductive material contains a disk-like liquid crystal compound as a curing agent and exhibits liquid crystallinity, heat resistance is improved.

Moreover, from the results of Example 35 and Example 51 to Example 53, it has been confirmed that in a case where the thermally conductive material contains boron nitride as an inorganic substance, thermal conductivity is further improved.

What is claimed is:

1. A thermally conductive material comprising:
   a cured substance of a disk-like compound, which has one or more reactive functional groups selected from the group consisting of a hydroxyl group, a carboxylic acid group, a carboxylic acid anhydride group, an amino group, a cyanate ester group, and a thiol group, and a crosslinking compound which has a group reacting with the reactive functional groups, and
   an inorganic substance,
   wherein in a case where the disk-like compound has a central ring that is a triphenylene ring, each of the reactive functional groups is a group selected from the group consisting of a hydroxyl group, a carboxylic acid group, a carboxylic acid anhydride group, an amino group, and a cyanate ester group,
   the crosslinking compound is an epoxy compound, which is a compound represented by Formula (E1),

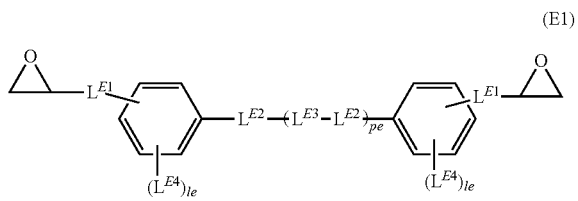

(E1)

in Formula (E1), $L^{E1}$'s each independently represent a single bond or a divalent linking group which is selected from the group consisting of —O—, —S—, —C(═O)—, —NH—, —CH═CH—, —C≡C—, —CH═N—, —N═CH—, —N═N—, an alkylene group which may have a substituent, or a group obtained by combining two or more groups among the above, $L^{E2}$'s each independently represent a single bond, —CH═CH—, —C(═O)—O—, —O—C(═O)—, —C(—CH₃)═CH—, —CH═C(—CH₃)—, —CH═N—, —N═CH—, —N═N—, —CC—, —N═N⁺(—O⁻)—, —N⁺(—O⁻)═N—, —CH═N⁺(—O⁻)—, —N⁺(—O⁻)═CH—, —CH═CH—C(═O)—, —C(═O)—CH═CH—, —CH═C(—CN)—, or —C(—CN)═CH—, $L^{E3}$ represents a 5-membered or 6-membered aromatic ring group which may have a substituent, or a 5-membered or 6-membered non-aromatic ring group which may have a substituent, pe represents an integer equal to or greater than 0, in a case where pe is an integer equal to or greater than 2, a plurality of groups represented by (-$L^{E3}$-$L^{E2}$-) may be the same as or different from each other, $L^{E4}$'s each independently represent a substituent, le's each independently represent an integer of 0 to 4, and in a case where le is an integer equal to or greater than 2, a plurality of $L^{E4}$'s may be the same as or different from each other.

2. The thermally conductive material according to claim 1,
wherein the disk-like compound is represented by Formula (1), $$M—(L^{c1}—Q)_{nc1} \quad (1)$$

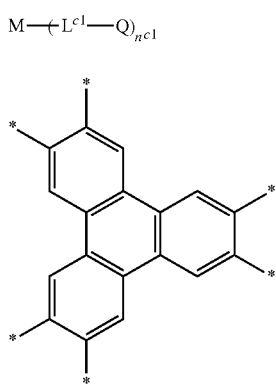

(CR4)

in the formula, M represents an $n^{C1}$ valent disk-like core portion,
$L^{c1}$ represents a divalent linking group,
Q represents a hydrogen atom or a substituent,
$n^{c1}$ represents an integer equal to or greater than 3,
one or more Q's represent reactive functional groups selected from the group consisting of a hydroxyl group, a carboxylic acid group, a carboxylic acid anhydride group, an amino group, and a cyanate ester group,
in a case where M is a triphenylene skeleton represented by Formula (CR4), one or more Q's represent reactive functional groups selected from the group consisting of a hydroxyl group, a carboxylic acid group, a carboxylic acid anhydride group, an amino group, and a cyanate ester group, and
in Formula (CR4), * represents a position of binding to a group represented by -$L^{c1}$-Q.

3. The thermally conductive material according to claim 2,
wherein the disk-like compound is a compound represented by Formula (D4),

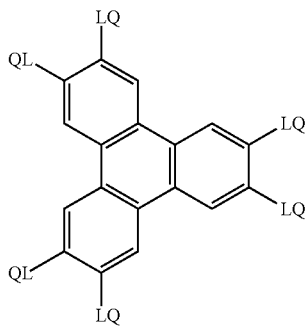

(D4)

L's each independently represent a divalent linking group,
Q's each independently represent a hydrogen atom or a substituent, and
one or more Q's represent reactive functional groups selected from the group consisting of a hydroxyl group, a carboxylic acid group, a carboxylic acid anhydride group, an amino group, and a cyanate ester group.

4. The thermally conductive material according to claim 2, wherein the number of the reactive functional groups the disk-like compound has is 3 to 6.

5. The thermally conductive material according to claim 1,
wherein the number of the reactive functional groups the disk-like compound has is 3 to 6.

6. The thermally conductive material according to claim 1,
wherein the disk-like compound has 3 to 6 groups selected from the group consisting of a hydroxyl group, a carboxylic acid group, and a carboxylic acid anhydride group.

7. The thermally conductive material according to claim 1,
wherein the inorganic substance is an inorganic nitride or an inorganic oxide.

8. The thermally conductive material according to claim 1,
wherein the inorganic substance is boron nitride.

9. The thermally conductive material according to claim 1 that is in the form of a sheet.

10. A device with a thermally conductive layer, comprising:
a device; and
a thermally conductive layer which is disposed on the device and contains the thermally conductive material according to claim 1.

11. The thermally conductive material according to claim 1,
wherein each of the reactive functional groups is a group selected from the group consisting of a hydroxyl group, a carboxylic acid group, a carboxylic acid anhydride group, an amino group, and a cyanate ester group.

12. A composition for forming a thermally conductive material, comprising;
a disk-like compound having one or more reactive functional groups selected from the group consisting of a hydroxyl group, a carboxylic acid group, a carboxylic acid anhydride group, an amino group, a cyanate ester group, and a thiol group;
a crosslinking compound having a group reacting with the reactive functional groups, and
an inorganic substance,
wherein in a case where the disk-like compound has a central ring that is a triphenylene ring, each of the reactive functional groups is a group selected from the group consisting of a hydroxyl group, a carboxylic acid group, a carboxylic acid anhydride group, an amino group, and a cyanate ester group,
the crosslinking compound is an epoxy compound, which is a compound represented by Formula (E1),

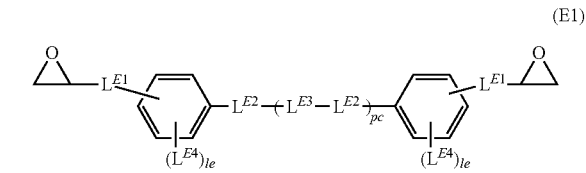

(E1)

in Formula (E1), $L^{E1}$'s each independently represent a single bond or a divalent linking group, which is selected from the group consisting of —O—, —S—, —C(=O)—, —NH—, —CH=CH—, —C≡C—, —CH=N—, —N=CH—, —N=N—, an alkylene group which may have a substituent, or a group obtained by combining two or more groups among the above, $L^{E2}$'s each independently represent a single bond, —CH=CH—, —C(=O)—O—, —O—C(=O)—, —C(—CH$_3$)=CH—, —CH=C(—CH$_3$)—, —CH=N—, —N=CH—, —N=N—, —CC—, —N=N$^+$(—O$^-$)—, —N$^+$(—O$^-$)=N—, —CH=N$^+$(—O$^-$)—, —N$^+$(—O$^-$)=CH—, —CH=CH—C(=O)—, —C(=O)—CH=CH—, —CH=C(—CN)—, or —C(—CN)=CH—, $L^{E3}$ represents a 5-membered or 6-membered aromatic ring group which may have a substituent, or a 5-membered or 6-membered non-aromatic ring group which may have a substituent, pe represents an integer equal to or greater than 0, in a case where pe is an integer equal to or greater than 2, a plurality of groups represented by (-$L^{E3}$-$L^{E2}$-) may be the same as or different from each other, $L^{E4}$'s each independently represent a substituent, le's each independently represent an integer of 0 to 4, and in a case where le is an integer equal to or greater than 2, a plurality of $L^{E4}$'s may be the same as or different from each other.

13. The composition for forming a thermally conductive material according to claim 12 that exhibits liquid crystallinity, comprising:

the disk-like compound that is liquid crystalline; and the crosslinking compound having a group reacting with the reactive functional groups.

14. The composition for forming a thermally conductive material according to claim 12, wherein each of the reactive functional groups is a group selected from the group consisting of a hydroxyl group, a carboxylic acid group, a carboxylic acid anhydride group, an amino group, and a cyanate ester group.

15. A disk-like liquid crystal compound that is a compound represented by Formula (D16),

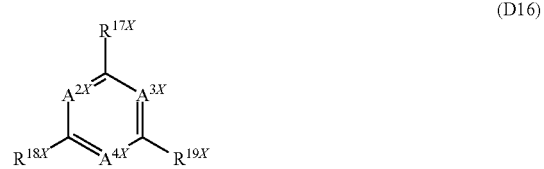

(D16)

in Formula (D16), $A^{2X}$, $A^{3X}$, and $A^{4X}$ each independently represent —CH= or —N=, $R^{17X}$, $R^{18X}$, and $R^{19X}$ each independently represent *—$X^{211X}$—($Z^{21X}$—$X^{212X}$)$_{n21X}$-$L^{21X}$-Q,

* represents a position of binding to a central ring, $X^{211X}$ and $X^{212X}$ each independently represent a single bond, —O—, —C(=O)—, —NH—, —OC(=O)—, —OC(=O)O—, —OC(=O)NH—, —OC(=O)S—, —C(=O)O—, —C(=O)NH—, —C(=O)S—, —NHC(=O)—, —NHC(=O)O—, —NHC(=O)NH—, —NHC(=O)S—, —S—, —SC(=O)—, —SC(=O)O—, —SC(=O)NH—, or —SC(=O)S—, $Z^{21X}$'s each independently represent a 5-membered or 6-membered aromatic ring group or a 5-membered or 6-membered non-aromatic ring group, $L^{21X}$ represents a single bond or a divalent linking group, Q's each independently represent a hydrogen atom or a substituent, one or more Q's represent reactive functional groups selected from a cyanate ester group, n21X represents an integer of 0 to 3, and in a case where n21X is equal to or greater than 2, a plurality of groups represented by ($Z^{21X}$—$X^{212X}$) may be the same as or different from each other.

16. The disk-like liquid crystal compound according to claim 15 that has a phase transition temperature, at which transition to a liquid crystal phase from a crystal phase occurs, equal to or lower than 180° C.

* * * * *